United States Patent
Kamo et al.

(10) Patent No.: US 10,739,577 B2
(45) Date of Patent: Aug. 11, 2020

(54) OBJECTIVE OPTICAL SYSTEM FOR ENDOSCOPE

(71) Applicant: OLYMPUS CORPORATION, Hachioji-shi, Tokyo (JP)

(72) Inventors: Yuji Kamo, Hino (JP); Hideyasu Takato, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 52 days.

(21) Appl. No.: 16/213,524

(22) Filed: Dec. 7, 2018

(65) Prior Publication Data

US 2019/0107706 A1 Apr. 11, 2019

Related U.S. Application Data

(63) Continuation of application No. PCT/JP2017/018864, filed on May 19, 2017.

(30) Foreign Application Priority Data

Jun. 20, 2016 (JP) ................ 2016-121631

(51) Int. Cl.
*G02B 23/24* (2006.01)
*A61B 1/00* (2006.01)
(Continued)

(52) U.S. Cl.
CPC ...... *G02B 23/2407* (2013.01); *A61B 1/00188* (2013.01); *G02B 9/20* (2013.01); *G02B 13/0045* (2013.01); *G02B 23/2438* (2013.01)

(58) Field of Classification Search
CPC ............. G02B 23/2407; G02B 23/243; G02B 23/2438; G02B 9/14; G02B 9/20; A61B 1/00188
(Continued)

(56) References Cited

U.S. PATENT DOCUMENTS 6,252,723 B1  6/2001  Nagaoka
8,130,454 B2 * 3/2012  Noguchi ............ G02B 23/2438
                                                                359/656
(Continued)

FOREIGN PATENT DOCUMENTS

JP  H11316339 A  11/1999
JP  2003043348 A  2/2003
(Continued)

OTHER PUBLICATIONS

International Search Report (ISR) dated Aug. 8, 2017 issued in International Application No. PCT/JP2017/018864.
(Continued)

*Primary Examiner* — Zachary W Wilkes
(74) *Attorney, Agent, or Firm* — Holtz, Holtz & Volek PC

(57) ABSTRACT

An objective optical system for endoscope includes a first lens group having a positive refractive power, a second lens group having a negative refractive power, and a third lens group having a positive refractive power. At a time of focusing, the first lens group and the third lens group are fixed, and the second lens group moves. The third lens group consists of a front group having a positive refractive power and a rear group having a positive refractive power. The front group includes one cemented lens and the rear group includes one single lens, and the following conditional expressions are satisfied:

$1 \le fG3f/fG3r \le 5$, $0.1 \le dG3fr/dG3r \le 1$, $-8 \le fc/rc \le -2$, and $-7 \le fG2/fG3 \le -2$.

9 Claims, 11 Drawing Sheets

(51) Int. Cl.
 *G02B 9/20* (2006.01)
 *G02B 13/00* (2006.01)
(58) Field of Classification Search
 USPC .................................................. 359/716, 661
 See application file for complete search history.

(56) References Cited

U.S. PATENT DOCUMENTS

| | | | |
|---|---|---|---|
| 8,427,762 B2* | 4/2013 | Maetaki | G02B 7/08 359/743 |
| 2010/0020408 A1 | 1/2010 | Noguchi | |
| 2011/0235192 A1 | 9/2011 | Uzawa et al. | |
| 2011/0299179 A1 | 12/2011 | Maetaki | |
| 2015/0085376 A1 | 3/2015 | Katakura | |
| 2015/0268460 A1 | 9/2015 | Takada | |
| 2018/0314054 A1* | 11/2018 | Takato | A61B 1/00 |

FOREIGN PATENT DOCUMENTS

| | | |
|---|---|---|
| JP | 2007054083 A | 3/2007 |
| JP | 4834799 B2 | 12/2011 |
| JP | 2011253050 A | 12/2011 |
| JP | 5148403 B2 | 2/2013 |
| WO | 2014088104 A1 | 6/2014 |

OTHER PUBLICATIONS

Japanese Office Action dated Feb. 21, 2018 issued in counterpart Japanese Application No. 2017-564937.
International Preliminary Report on Patentability (IPRP) (and English language translation thereof) dated Jan. 3, 2019 issued in counterpart International Application No. PCT/JP2017/018864.

* cited by examiner

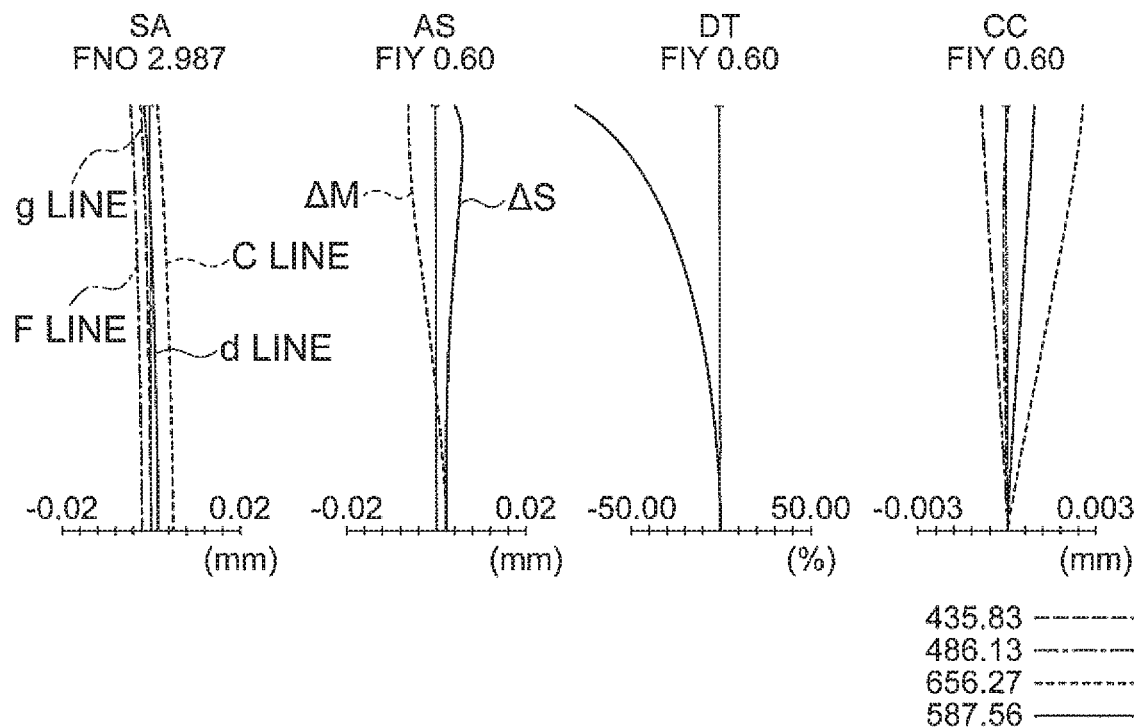
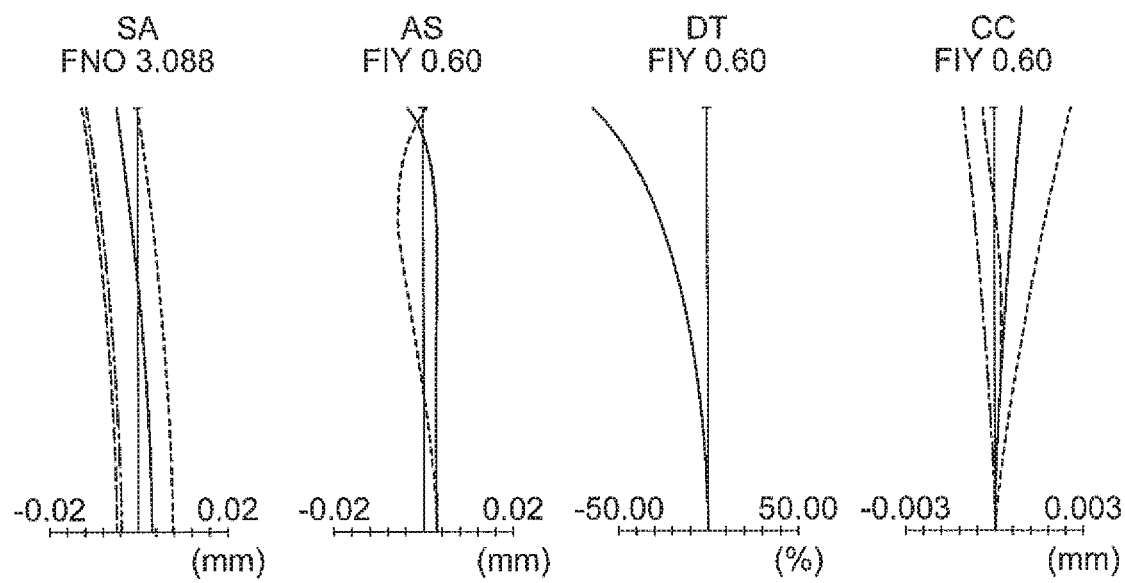

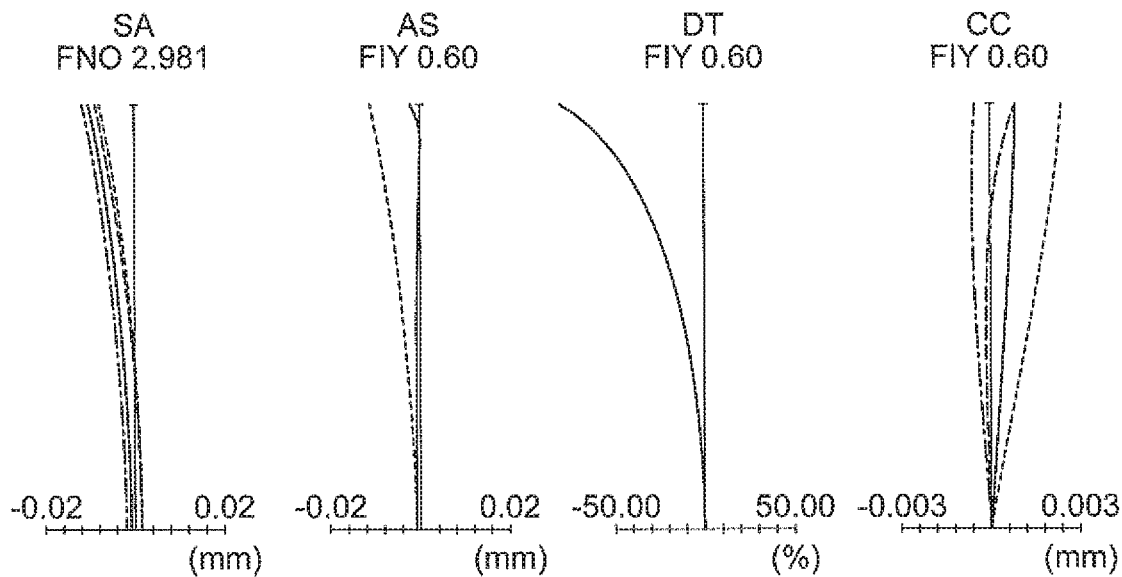
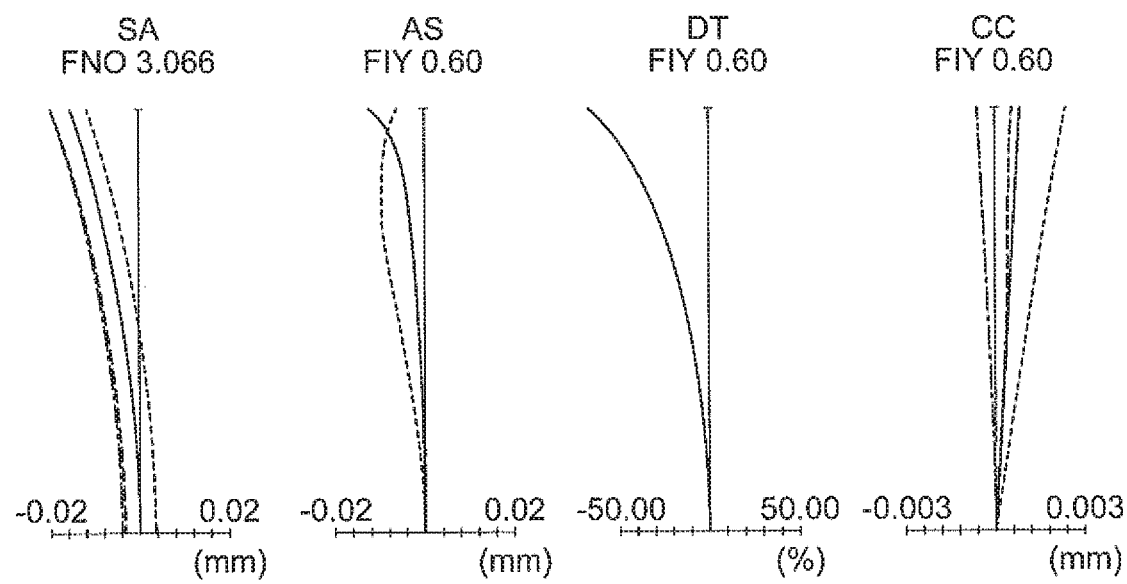

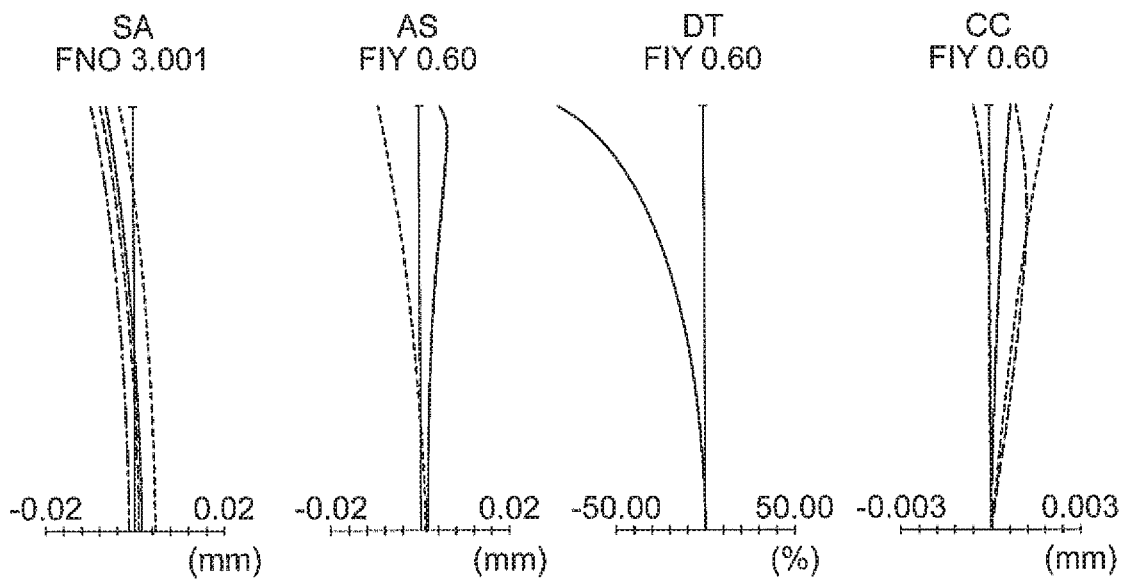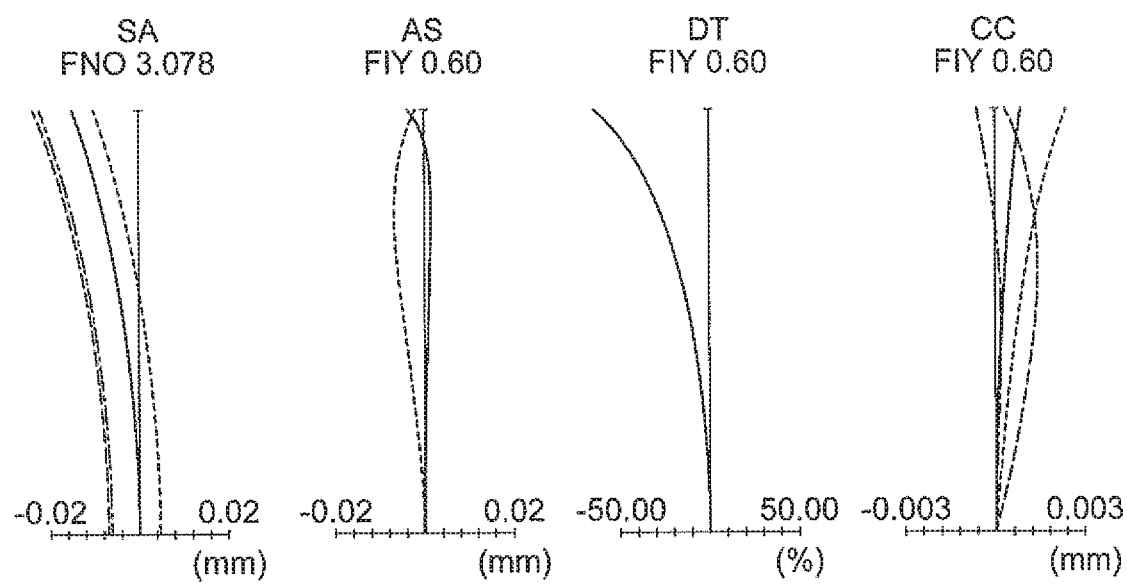

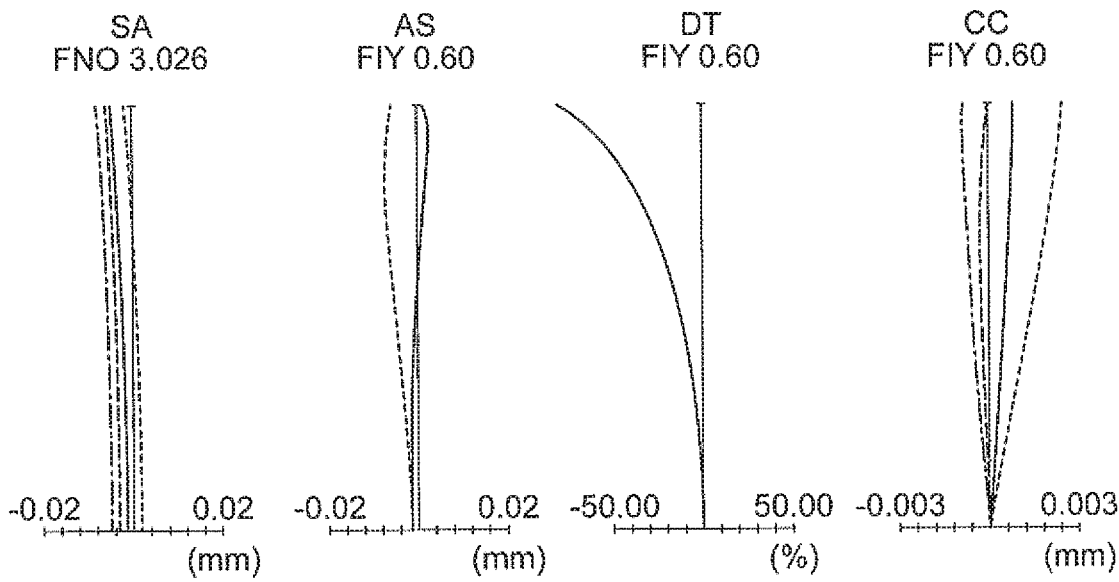
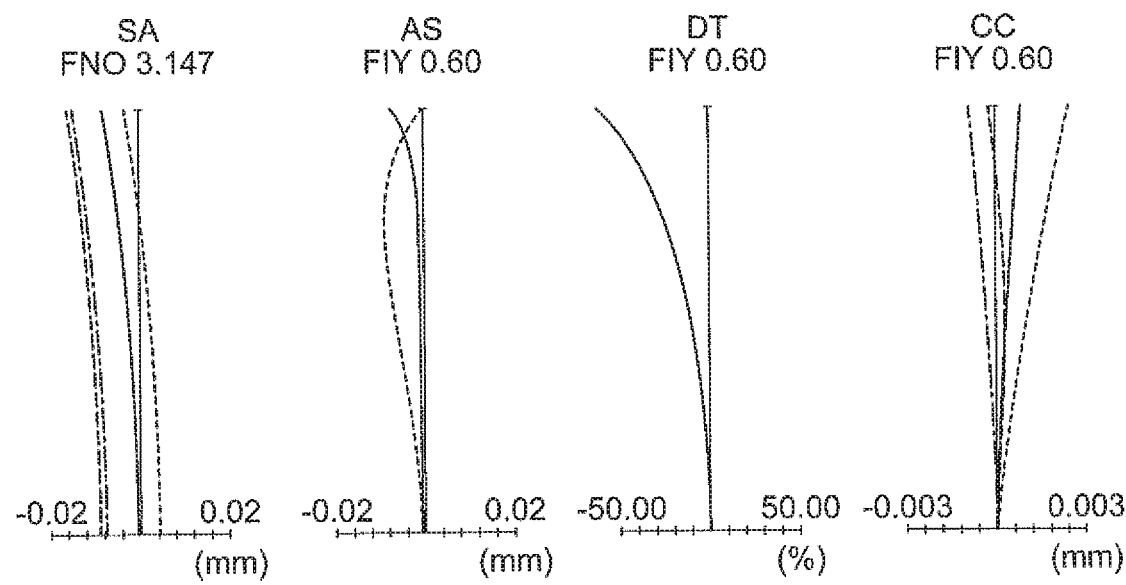

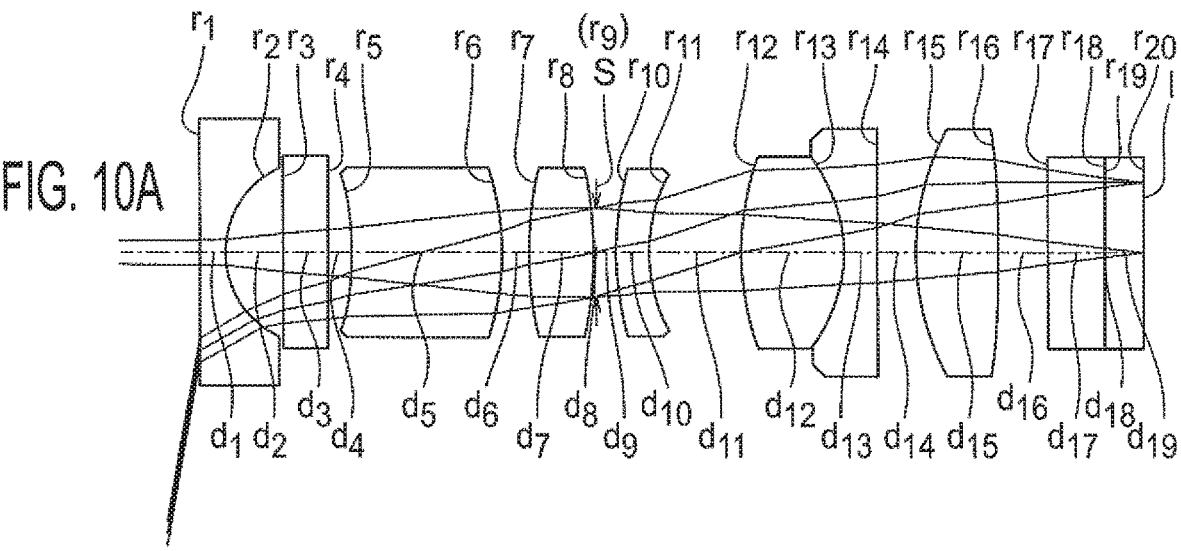
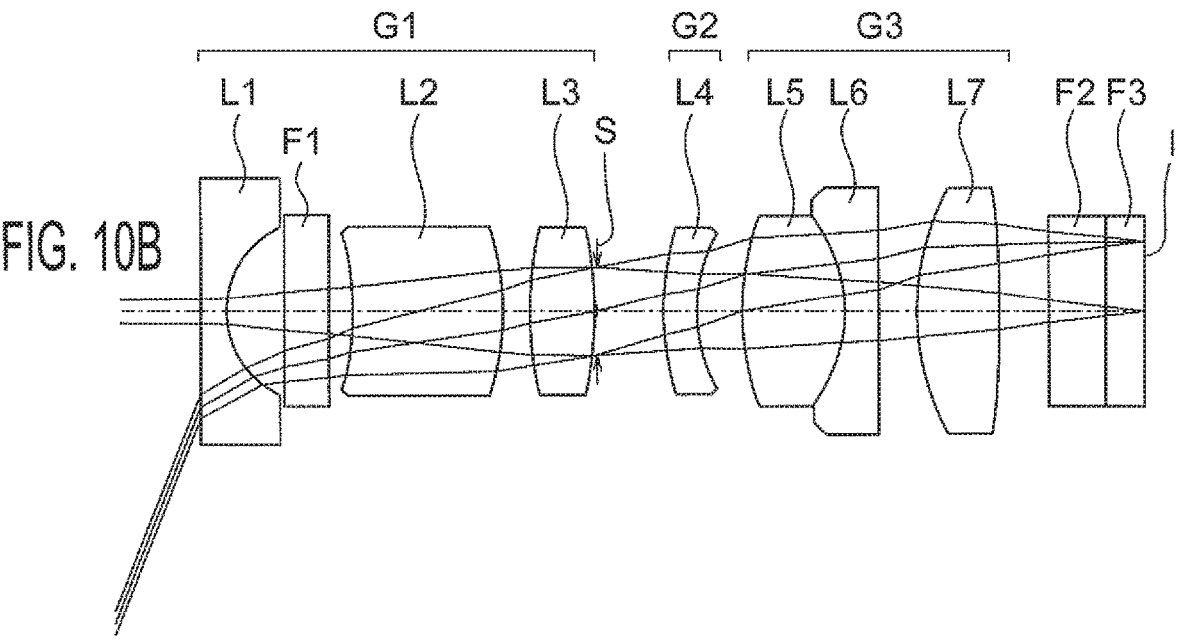

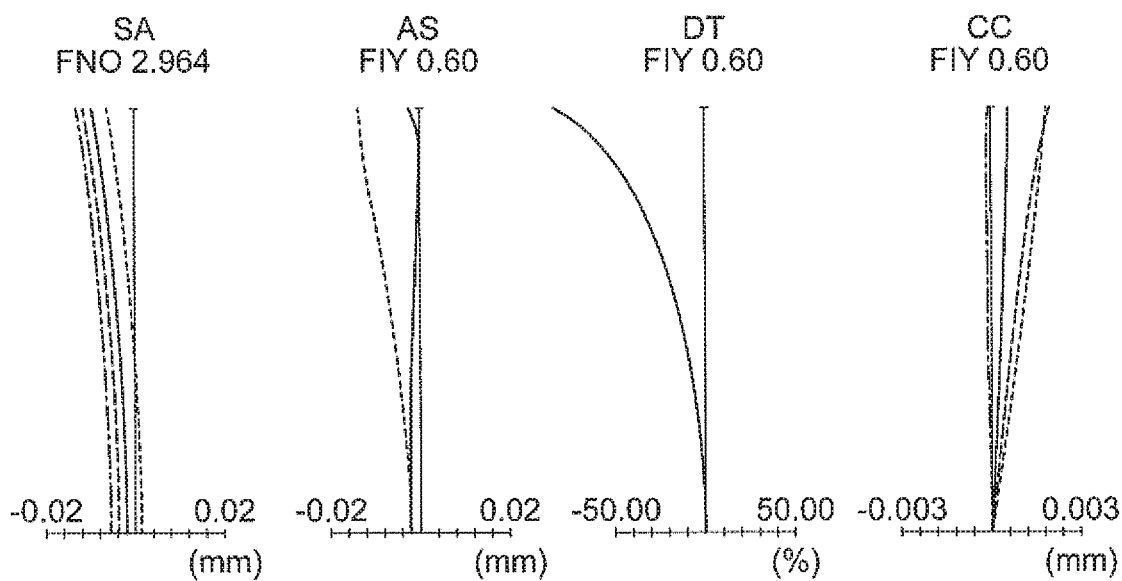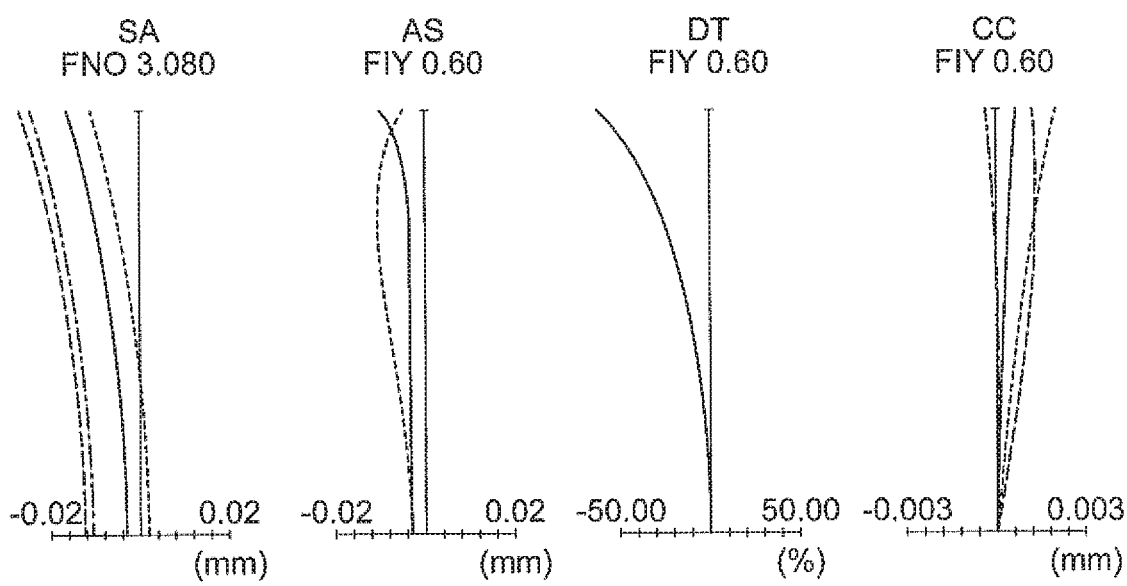

OBJECTIVE OPTICAL SYSTEM FOR ENDOSCOPE

CROSS-REFERENCE TO RELATED APPLICATION

The present application is a continuation application of PCT/JP2017/018864 filed on May 19, 2017 which is based upon and claims the benefit of priority from Japanese Patent Application No. 2016-121631 filed on Jun. 20, 2016; the entire contents of which are incorporated herein by reference.

BACKGROUND OF THE INVENTION

Field of the Invention

The present invention relates to an objective optical system, and to an objective optical system for endoscope that can be used in an endoscope apparatus used in the medical field and the industrial field for example.

Description of the Related Art

An endoscope is an apparatus that is widely used in the medical field and the industrial field. Particularly, in the medical field, endoscopes are used for a diagnosis and treatment of a part to be observed. For the diagnosis and treatment, images achieved by an endoscope inserted inside a body cavity are used.

In an objective optical system for endoscope, by setting appropriate F-number and focusing position, a focused image from a near point up to a far point is formed. Moreover, in an objective optical system, small-sizing of a lens diameter and shortening of an overall length of an optical system is carried out. By doing so, it is possible to make an insertion portion thin. As a result, it is possible to reduce pain at a time of insertion and to realize an insertion portion that can be turned in small radius. In recent years, endoscopes with even higher image quality and smaller size have been sought.

As an objective optical system for endoscope, an objective optical system having a wide depth of field and an objective optical system which enables an observation with a high magnification have been proposed. In the objective optical system which enables an observation with a high magnification, focusing and zooming are carried out by moving a lens group. As such objective optical system, objective optical systems described in Japanese Patent Application Laid-open Publication No. Hei 11-316339, Japanese Patent No. 4834799 Publication, Japanese Patent No. 5148403 Publication, and Japanese Patent No. 5580956 Publication are available.

In general, by increasing the number of pixels of an image pickup element, it is possible to achieve a high-quality image. When an image pickup surface is made large-sized in accordance with the increase in the number of pixels, a height of an image formed on the image pickup surface has to be made high. However, when the image height becomes high, an optical system also becomes large. In this case, it becomes difficult to make an optical system small. Consequently, in an image pickup element to be used in an endoscope, by making a pixel pitch small with the size of the image pickup element same as it has been, a method of achieving a high-quality image while maintaining the small-size has been carried out in many cases.

However, when the pixel pitch becomes small, in an objective optical system, a permissible circle of confusion is sought to be made further smaller. For this, an objective optical system having a high optical performance becomes necessary. The permissible circle of confusion has a large effect of diffraction. Therefore, it is necessary to make the objective optical system an optical system with a small F-number.

In general, when the F-number becomes small, an aberration correction becomes difficult. For correcting an aberration favorably, the number of lenses is to be increased or the overall length of the optical system is to be made long. Therefore, the optical system tends to be large in size. Thus, when the pixel pitch is made small with the size of the image pickup element same as it has been, it is not possible to achieve small-sizing and high performance of the optical system simply.

Furthermore, when the F-number becomes small, the optical system becomes weak with respect to a manufacturing variation. In other words, an optical performance is susceptible to be degraded due to errors such as an error in a radius of curvature of a lens component, an error in a lens thickness, a shift error and a tilt error in a mechanical frame and a lens at a time of assembling the optical system. For such reason, it is desired that an optical system has a large tolerable error amount.

Particularly, regarding focusing that is carried out at a time of manufacturing, the tolerable error amount is determined by the pixel pitch and the permissible circle of confusion which is almost determined by the F-number. For instance, when the tolerable error of focusing is in the range of 3 μm to 5 μm, it is significantly small as the tolerable error amount.

When the focusing is finished, the lenses and the image pickup element are fixed by an adhesive. At this time, with the hardening of the adhesive, there is a shift in positions of lenses and a position of the image pickup element. When the tolerable amount is small as mentioned above, the adhesive is sought to be such that the amount of shift due to the hardening of the adhesive is small. However, there are cases in which it is difficult to deal with by the adhesive. For such reason, with regard to the focusing error, in an optical system, it is desired that the tolerable error amount is large.

SUMMARY OF THE INVENTION

An objective optical system according to at least some embodiments of the present invention comprises in order from an object side:

a first lens group having a positive refractive power, a second lens group having a negative refractive power, and a third lens group having a positive refractive power, wherein at a time of focusing to an object point at a short distance, the first lens group and the third lens group are fixed, and the second lens group moves, and the third lens group consists of a front group having a positive refractive power and a rear group having a positive refractive power, and the front group includes one cemented lens and the rear group includes one single lens, and the following conditional expressions (1-1), (1-2), (4-1), and (4-2) are satisfied:

$$1 \leq fG3f/fG3r \leq 5 \tag{1-1}$$

$$0.1 \leq dG3fr/dG3r \leq 1 \tag{1-2}$$

$$-8 \leq fc/rc \leq -2 \tag{4-1}$$

$$-7 \leq fG2/fG3 \leq -2 \tag{4-2}$$

where, fG3f denotes a focal length of the front group, fG3r denotes a focal length of the rear group, dG3fr denotes a distance along an optical axis from a surface nearest to an image of the front group up to a surface nearest to an object of the rear group, dG3r denotes a total thickness along the optical axis of the rear group, fc denotes a focal length of the cemented lens, rc denotes a radius of curvature of a cemented surface of the cemented lens, fG2 denotes a focal length of the second lens group, and fG3 denotes a focal length of the third lens group.

BRIEF DESCRIPTION OF THE DRAWINGS

FIG. 3A, FIG. 3B, FIG. 3C, FIG. 3D, FIG. 3E, FIG. 3F, FIG. 3G, and FIG. 3H are aberration diagrams of the objective optical system for endoscope of the example 1;

FIG. 5A, FIG. 5B, FIG. 5C, FIG. 5D, FIG. 5E, FIG. 5F, FIG. 5G, and FIG. 5H are aberration diagrams of the objective optical system for endoscope of the example 2;

FIG. 7A, FIG. 7B, FIG. 7C, FIG. 7D, FIG. 7E, FIG. 7F, FIG. 7G, and FIG. 7H are aberration diagrams of the objective optical system for endoscope of the example 3;

FIG. 9A, FIG. 9B, FIG. 9C, FIG. 9D, FIG. 9E, FIG. 9F, FIG. 9G, and FIG. 9H are aberration diagrams of the objective optical system for endoscope of the example 4;

FIG. 10A and FIG. 10B are cross-sectional views of an objective optical system for endoscope of an example 5; and FIG. 11A, FIG. 11B, FIG. 11C, FIG. 11D, FIG. 11E, FIG. 11F, FIG. 11G, and FIG. 11H are aberration diagrams of the objective optical system for endoscope of the example 5.

DETAILED DESCRIPTION OF THE INVENTION

Reasons for and an effect of adopting such arrangements for an objective optical system for endoscope according to the present embodiment will be described below by using the accompanying diagrams. However, the present invention is not restricted to the embodiment described below.

An objective optical system for endoscope according to the present embodiment enables to carry out a normal observation and a close observation with one optical system in an endoscopic observation. For this, the objective optical system is formed of a plurality of lens groups, and at least one lens group of the plurality of lens groups moves on an optical axis. Accordingly, it is possible to carry out the normal observation when focused to an object point at a long distance, and the close observation when focused to an object point at a close distance.

The objective optical system for endoscope according to the present embodiment includes in order from an object side, a first lens group having a positive refractive power, a second lens group having a negative refractive power, and a third lens group having a positive refractive power, and at a time of focusing to an object point at a close distance, the first lens group and the third lens groups are fixed, and the second lens group moves, and the third lens group includes a front group having a positive refractive power and a rear group having a positive refractive power, and each of the front group and the rear group includes one single lens or one cemented lens, and the following conditional expressions (1-1) and (1-2), are satisfied:

$$1 \leq fG3f/fG3r \leq 5 \tag{1-1}$$

$$0.1 \leq dG3fr/dG3r \leq 1 \tag{1-2}$$

where, fG3f denotes a focal length of the front group, fG3r denotes a focal length of the rear group, dG3fr denotes a distance along an optical axis from a surface nearest to an image of the front group up to a surface nearest to an object of the rear group, and dG3r denotes a total thickness along the optical axis of the rear group.

Figure 1:
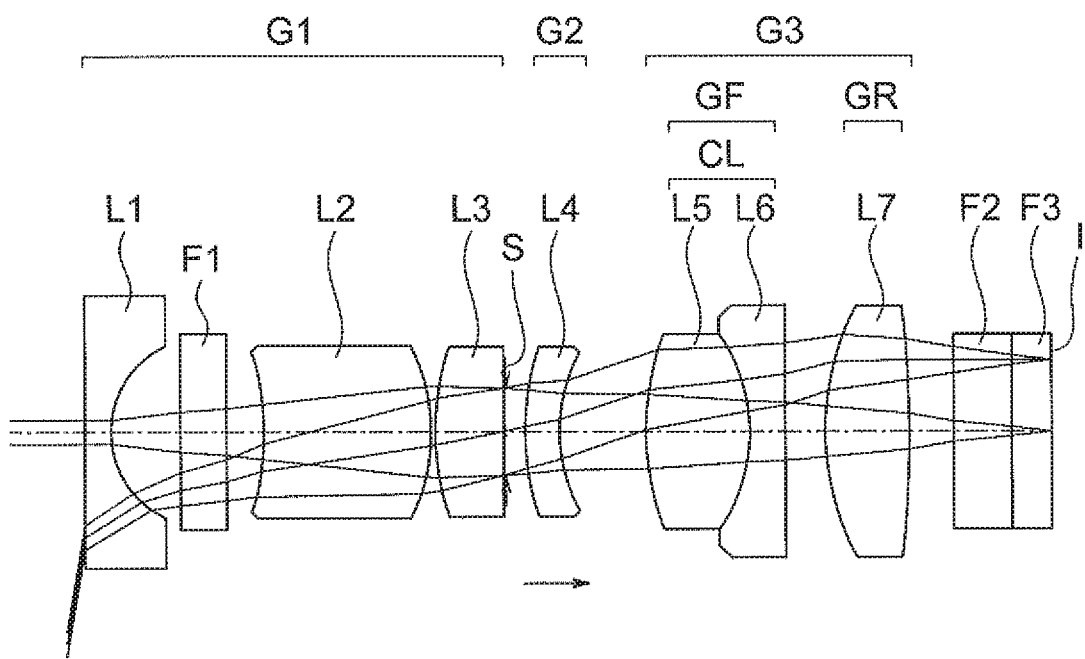
FIG. 1 is a cross-sectional view showing a specific arrangement of an objective optical system for endoscope of the present embodiment.

The objective optical system for endoscope of the present embodiment will be described below. FIG. 1 is a diagram showing the objective optical system for endoscope of the present embodiment. As shown in FIG. 1, the objective optical system for endoscope of the present embodiment includes in order from an object side, a first lens group G1 having a positive refractive power, a second lens group G2 having a negative refractive power, and a third lens group G3 having a positive refractive power.

In an objective optical system for endoscope, a focusing function is sought to be imparted to an optical system while small-sizing the optical system. For fulfilling this requirement, in the objective optical system for endoscope of the present embodiment, an optical system is let to include three lens groups, and furthermore, the refractive power of the three lens groups is let to be a positive refractive power, a negative refractive power, and a positive refractive power in order from the object side.

Accordingly, it is possible to distribute the positive refractive power to two lens groups, and moreover, the negative refractive power is positioned between the two positive refractive powers. As a result, an aberration fluctuation at the time of focusing becomes small, and it is possible to form an objective optical system for endoscope having a high imaging performance.

The first lens group G1 includes a negative lens L1, a positive lens L2, and a positive lens L3. The second lens group G2 includes a negative lens L4. The third lens group G3 includes a front group GF having a positive refractive power and a rear group GR having a positive refractive power.

In FIG., the front group GF includes a cemented lens CL. The cemented lens CL includes a positive lens L5 and a negative lens L6. The rear group GR includes a positive lens L7.

A first plane parallel plate F1 is disposed between the negative lens L1 and the positive lens L2. It is possible to dispose the first plane parallel plate F1 at an arbitrary position in the objective optical system for endoscope. A second plane parallel plate F2 and a third plane parallel plate F3 are disposed on an image side of the positive lens L7. The second plane parallel plate F2 and the third plane parallel plate F3 are cemented.

The second plane parallel plate F2 and the third plane parallel plate F3 are a cover glass, and a cover glass of an image pickup element. An image pickup element (not shown in the diagram) is disposed on the image side of the third plane parallel plate F3. An image-side surface of the third plane parallel plate F3 is an image plane I. An image pickup surface of the image pickup element coincides with the image-side surface of the third plane parallel plate F3.

An aperture stop S is disposed between the first lens group G1 and the second lens group G2. More specifically, the aperture stop S is disposed near the image-side surface of the positive lens L3.

At the time of focusing, the first lens group G1 and the third lens group G3 are fixed, and the second lens group G2 moves. At the time of focusing from the object point at a close distance to the object point at a long distance, the second lens group G2 moves toward the image side.

By moving the second lens group G2 at the time of focusing, it is possible to zoom effectively with a small amount of movement. At this time, by letting the first lens group G1 and the third lens group G3 to be fixed, it is possible to make a lens frame simple. As a result, thinning of an outer diameter of an endoscope becomes possible.

It is possible to combine the objective optical system for endoscope of the present embodiment with an image pickup element. In recent years, making the number of pixels of an image pickup element large has been progressing. With the progress in making the number of pixels large, a pixel pitch becomes small. As the pixel pitch becomes small, a permissible circle of confusion in an optical system also becomes small.

While assembling an optical system, an adjustment for making a position of an object image and a position of an image pickup surface coincide (hereinafter, referred to as 'focus adjustment') is carried out. For capturing a focused object image, it is necessary that the focus adjustment has been carried out with a high degree of accuracy. In the focus adjustment, a movement of lenses, a movement of the image pickup element, or a movement of the lenses and the image pickup element are carried out. When the permissible circle of confusion in the optical system is small, even higher precision is sought in the focus adjustment.

As mentioned above, in the objective optical system for endoscope of the present embodiment, the third lens group G3 includes the front group GF and the rear group GR. Moreover, in adjusting the position of the object image and the image pickup surface, the rear group GR and the image pickup element are moved.

By making such arrangement, when the rear group GR and the image pickup element have moved together, a longitudinal magnification of the optical system becomes small. Consequently, it is possible to reduce error sensitivity at the time of focus adjustment. As a result, it is possible to carry out the focus adjustment with a high degree of accuracy and easily.

It is preferable that each of the front group GF and the rear group GR include one single lens or one cemented lens. When such arrangement is made, it is possible to simplify the lens frame and to shorten the overall length of the optical system.

The objective optical system for endoscope of the present embodiment has the abovementioned arrangement and conditional expressions (1-1) and (1-2) are satisfied.

In a case of falling below a lower limit value of conditional expression (1-1), the refractive power of the front group becomes excessively large or the refractive power of the rear group becomes excessively small. When the refractive power of the front group becomes excessively large, a coma and an astigmatism are deteriorated. When the refractive power the rear group becomes excessively small, an imaging performance is degraded due to an error at the time of focus adjustment.

In a case of exceeding an upper limit value of conditional expression (1-1), the refractive power of the front group becomes excessively small or the refractive power of the rear group becomes excessively large. When the refractive power of the front group becomes excessively small, a height of a light ray passing through the third lens group becomes high. As a result, a lens diameter in the third lens group becomes large. When the refractive power of the rear group becomes excessively large, the coma and the astigmatism are deteriorated.

In a case of exceeding an upper limit value of conditional expression (1-2), the overall length of the optical system becomes long or the height of a light ray passing through the third lens group becomes high. When the height of a light ray passing through the third lens group becomes high, the lens diameter in the third lens group becomes large.

In a case of falling below a lower limit value of conditional expression (1-2), a distance between the third lens group and the aperture stop becomes excessively short. In this case, an angle of incidence of a light ray incident on the image plane becomes large. In other words, it becomes difficult to make an arrangement of the optical system a telecentric arrangement on the image side or an arrangement close to the telecentric arrangement. Consequently, an imaging performance is susceptible to be degraded with respect to the manufacturing error of the rear group.

It is preferable that the following conditional expression (1-1)' be satisfied instead of conditional expression (1-1).

$$1.2 \leq fG3f/fG3r \leq 4 \qquad (1\text{-}1)'$$

It is more preferable that the following conditional expression (1-1)" be satisfied instead of conditional expression (1-1).

$$1.35 \leq fG3f/fG3r \leq 3.5 \qquad (1\text{-}1)''$$

It is preferable that the following conditional expression (1-2)' be satisfied instead of conditional expression (1-2).

$$0.2 \leq dG3fr/dG3r \leq 0.9 \qquad (1\text{-}2)'$$

It is more preferable that the following conditional expression (1-2") be satisfied instead of conditional expression (1-2).

$$0.3 \leq dG3fr/dG3r \leq 0.8 \qquad (1\text{-}2)''$$

In a case of satisfying conditional expression (1-1), the refractive power of the rear group is either equal to the refractive power of the front group or larger than the refractive power of the front group. It is preferable to let the refractive power of the rear group to be larger than the refractive power of the front group.

However, when the refractive power of the rear group becomes large, the rear group has a large effect of the manufacturing error. A decentering error is an example of the manufacturing error. The decentering error occurs due to a shift of a lens or a lens tilt. Particularly, when the decentering error is large, the degradation of an imaging performance becomes substantial.

For reducing the effect due to the decentering error, it is desirable to make an arrangement such that an angle of incidence of a principal light ray with respect to the image plane becomes small. When such arrangement is made, the arrangement of the optical system becomes the telecentric arrangement on the image side or the arrangement close to the telecentric arrangement. As a result, the degradation of an imaging performance becomes small.

For making the arrangement of the optical system the telecentric arrangement on the image side, it is preferable to make a distance from the aperture stop up to the rear group as long as possible. For such reason, in a case in which the refractive power of the rear group is made larger than the refractive power of the front group, it is preferable to satisfy the abovementioned conditional expression (1-2) in particular.

According to the objective optical system for endoscope of the present embodiment, it is possible to realize an objective optical system having a small size and a high imaging performance. Moreover, it is possible to realize an objective optical system for endoscope which is strong with respect to the manufacturing error. In other words, in the objective optical system for endoscope of the present embodiment, with regard to various errors that occur at the time of manufacturing, it is possible to make a tolerable error amount large.

In the objective optical system for endoscope according to the present embodiment, it is preferable that the following conditional expression (2) be satisfied:

$$0.42 \leq fG1/fG3r \leq 0.9 \quad (2)$$

where,
fG1 denotes a focal length of the first lens group, and
fG3r denotes the focal length of the rear group.

It is preferable to make the refractive power of the rear group comparatively larger than the refractive power of the front group. However, in this case, when the refractive power of the first lens group is not set appropriately, it is not possible to correct an aberration at a periphery of an image favorably. For such reason, it is preferable to satisfy conditional expression (2).

In a case of exceeding an upper limit value of conditional expression (2), the refractive power of the first lens group becomes excessively small or the refractive power of the rear group becomes excessively large. When the refractive power of the first lens group becomes excessively small, the overall length of the optical system becomes long. When the refractive power of the rear group becomes excessively large, the coma and the astigmatism are deteriorated.

In a case of falling below a lower limit value of conditional expression (2), the refractive power of the first lens group becomes excessively large or the refractive power of the rear group becomes excessively small. When the refractive power of the first lens group becomes excessively large, an amount of occurrence of various aberrations in the first lens group becomes excessively large. In this case, it is not possible to correct, particularly, the coma, the astigmatism, and a chromatic aberration of magnification in the third lens group. Consequently, it is not possible to correct an aberration favorably in the overall optical system. When the refractive power of the rear group becomes excessively small, an imaging performance is degraded due to an error at the time of focus adjustment.

It is more preferable that the following conditional expression (2)' be satisfied instead of conditional expression (2).

$$0.45 \leq fG1/fG3r \leq 0.8 \quad (2)'$$

It is even more preferable that the following conditional expression (2)" be satisfied instead of conditional expression (2).

$$0.48 \leq fG1/fG3r \leq 0.7 \quad (2)''$$

In the objective optical system for endoscope according to the present embodiment, it is preferable that the following conditional expression (3) be satisfied:

$$-2 \leq fG2/fG3f \leq -1.05 \quad (3)$$

where,
fG2 denotes a focal length of the second lens group, and
fG3f denotes the focal length of the front group.

The refractive power of the front group becomes relatively small with respect to the refractive power of the rear group. Therefore, when the refractive power of the second lens group is not set appropriately, it is not possible to carry out zooming effectively or it is not possible to balance various aberrations. For such reason, it is preferable to satisfy conditional expression (3).

In a case of exceeding an upper limit value of conditional expression (3), the refractive power of the second lens group becomes excessively large or the refractive power of the rear group becomes excessively small. When the refractive power of the second lens group becomes excessively large, a spherical aberration, the coma, and the astigmatism are deteriorated. When the refractive power of the rear group becomes excessively small, an imaging performance is deteriorated due to an error at the time of focus adjustment.

In a case of falling below a lower limit value of conditional expression (3), the refractive power of the second lens group becomes excessively small or the refractive power of the rear group becomes excessively large. When the refractive power of the second lens group becomes excessively small, an amount of movement of the second lens group becomes large. As a result, the overall length of the optical system becomes long. When the refractive power of the rear group becomes excessively large, the coma and the astigmatism are corrected excessively.

In the objective optical system for endoscope according to the present embodiment, it is preferable that the following conditional expressions (4-1) and (4-2) be satisfied:

$$-8 \leq fc/rc \leq -2 \quad (4-1)$$

$$-7 \leq fG2/fG3 \leq -2 \quad (4-2)$$

where,
fc denotes a focal length of the cemented lens in the third lens group,
rc denotes a radius of curvature of a cemented surface of the cemented lens in the third lens group,
fG2 denotes the focal length of the second lens group, and
fG3 denotes a focal length of the third lens group.

In a case in which the chromatic aberration of magnification occurs in the first lens group, it is necessary to correct the chromatic aberration of magnification in another lens group. For correcting the chromatic aberration of magnification in the third lens group, it is preferable to dispose a cemented lens in the third lens group.

Moreover, it is preferable that the error sensitivity at the time of focus adjustment can be lowered. Therefore, it is preferable to make an arrangement in the third lens group such that the overall length of the optical system does not become long, while varying the balance of the refractive power. For such reason, it is preferable to satisfy conditional expressions (4-1) and (4-2).

In a case of exceeding an upper limit value of conditional expression (4-1), the coma and chromatic aberration at a cemented surface are corrected excessively, or a radius of curvature of the cemented surface becomes excessively small. When the radius of curvature of the cemented surface becomes excessively small, a workability of a lens is degraded. As a result, a cost increases.

In a case of falling below a lower limit value of conditional expression (4-1), a chromatic aberration correction effect by cementing is reduced. Consequently, the chromatic aberration of magnification is deteriorated.

In a case of exceeding an upper limit value of conditional expression (4-1), the refractive power of the second lens group becomes excessively large, or it is not possible to secure a back focus, or the refractive power of the third lens group becomes excessively small. When the refractive power of the second lens group becomes excessively large, the spherical aberration, the coma, and the astigmatism are deteriorated. When the refractive power of the third lens group becomes excessively small, the overall length of the optical system becomes long or it is not possible to correct the coma and the astigmatism that occur in the first lens group.

In a case of falling below a lower limit value of conditional expression (4-2), the refractive power of the second lens group becomes excessively small or the refractive power of the third lens group becomes excessively large. When the refractive power of the second lens group becomes excessively small, an amount of movement of the second lens group becomes large. As a result, the overall length of the optical system becomes long. When the refractive power of the third lens group becomes excessively large, the coma and the astigmatism are deteriorated.

It is more preferable that the following conditional expression (4-1)' be satisfied instead of conditional expression (4-1)

$$-7 \leq fc/rc \leq -2.2 \quad (4\text{-}1)'$$

It is even more preferable that the following conditional expression (4-1)" be satisfied instead of conditional expression (4-1).

$$-6 \leq fc/rc \leq -2.4 \quad (4\text{-}1)''$$

It is more preferable that the following conditional expression (4-2)' be satisfied instead of conditional expression (4-2).

$$5.5 \leq fG2/fG3 \leq -2.1 \quad (4\text{-}2)'$$

It is even more preferable that the following conditional expression (4-2)" be satisfied instead of conditional expression (4-2).

$$-4.5 \leq fG2/fG3 \leq -2.2 \quad (4\text{-}2)''$$

In the objective optical system for endoscope according to the present embodiment, it is preferable that the first lens group include an object-side negative lens which is disposed nearest to the object, and the following conditional expressions (5-1) and (5-2) be satisfied:

$$0.5 \leq fG1/fG23 \leq 1 \quad (5\text{-}1)$$

$$0.2 \leq f/rG1nr \leq 1 \quad (5\text{-}2)$$

where, fG1 denotes the focal length of the first lens group, fG23 denotes a combined focal length of the second lens group and the third lens group, f denotes a focal length of an overall objective optical system for endoscope, and rG1nr denotes a radius of curvature of an image-side surface of the object-side negative lens, and here the combined focal length and the focal length of the overall objective optical system for endoscope are focal lengths in a normal state.

An aberration that occurs in the first lens group is corrected in the second lens group and the third lens group. Therefore, when an amount of aberration that occurs in the first lens group becomes excessively large, it is not possible to correct the aberration thoroughly in the second lens group and the third lens group. To suppress an increase in the aberration that occurs in the first lens group, it is preferable to satisfy conditional expressions (5-1) and (5-2). Let the normal state be a state in which a focal point is on a far-point side with respect to the close state.

In a case of exceeding an upper limit value of conditional expression (5-1), the refractive power of the first lens group becomes excessively weak or the combined refractive power of the second lens group and the third lens group becomes excessively strong. When the refractive power of the first lens group becomes excessively weak, the overall length of the optical system becomes long. When the combined refractive power of the second lens group and the third lens group becomes excessively strong, the spherical aberration and the coma are corrected excessively.

In a case of falling below a lower limit value of conditional expression (5-1), the refractive power of the first lens group becomes excessively large or the combined refractive power of the second lens group and the third lens group becomes excessively small. When the refractive power of the first lens group becomes excessively large, an amount of the coma and the astigmatism becomes substantial. In this case, it is not possible to correct the coma and the astigmatism thoroughly in the second lens group and the third lens group. When the combined refractive power of the second lens group and the third lens group becomes excessively small, the overall length of the optical system becomes long or a lens diameter becomes large.

In a case of exceeding an upper limit value of conditional expression (5-2), the radius of curvature of the image-side surface of the object-side negative lens becomes excessively small. Consequently, an amount of the coma and the chromatic aberration of magnification becomes substantial.

In a case of falling below a lower limit value of conditional expression (5-2), the overall length of the optical system becomes long or a lens diameter of the object-side negative lens becomes large. When the lens diameter of the object-side negative lens becomes large, it is not possible to make the optical system small-sized.

It is more preferable that the following conditional expression (5-1)' be satisfied instead of conditional expression (5-1).

$$0.51 \leq fG1/fG23 \leq 0.9 \quad (5\text{-}1)'$$

It is even more preferable that the following conditional expression (5-1)" be satisfied instead of conditional expression (5-1).

$$0.52 \leq fG1/fG23 \leq 0.8 \quad (5\text{-}1)''$$

It is more preferable that the following conditional expression (5-2)' be satisfied instead of conditional expression (5-2).

$$0.4 \leq f/rG1nr \leq 0.9 \quad (5\text{-}2)'$$

It is even more preferable that the following conditional expression (5-2)" be satisfied instead of conditional expression (5-2).

$$0.55 \leq f/rG1nr \leq 0.85 \qquad (5\text{-}2)''$$

In the objective optical system for endoscope according to the present embodiment, it is preferable that the front group include a cemented lens, and the cemented lens include a front-side positive lens, and the rear group include a rear-side positive lens, and the following conditional expression (6) be satisfied:

$$0.38 \leq fG3pf/fG3pr \leq 0.9 \qquad (6)$$

where, fG3pf denotes a focal length of the front-side positive lens, and fG3pr denotes a focal length of the rear-side positive lens.

By the front group including the cemented lens and the rear group including the single lens, it is possible to make further smaller an effect of focus variation by the manufacturing error. By the rear group including the single lens as well as by making the positive refractive power large, it is possible to use the cemented lens for suppressing mainly an occurrence of the chromatic aberration of magnification. As a result, it is possible to make an effect of the manufacturing error small while maintaining a high imaging performance.

The third lens group includes the front-side positive lens and the rear-side positive lens. The front-side positive lens and the rear-side positive lens are involved in the effect of the manufacturing error and an aberration performance. Therefore, it is necessary to balance the refractive power of the front-side positive lens and the refractive power of the rear-side positive lens. For such reason, it is preferable that conditional expression (6) be satisfied.

Ina case of exceeding an upper limit value of conditional expression (6), the refractive power of the front-side positive lens becomes excessively small or the refractive power of the rear-side positive lens becomes excessively large. When the refractive power of the front-side positive lens becomes excessively small, the chromatic aberration of magnification is corrected inadequately. When the refractive power of the rear-side positive lens becomes excessively large, an imaging performance is degraded substantially due to an error of lens decentering in a direction of shift.

In a case of falling below a lower limit value of conditional expression (6), the refractive power of the front-side positive lens becomes excessively large or the refractive power of the rear-side positive lens becomes excessively small. When the refractive power of the front-side positive lens becomes excessively large, the spherical aberration and the coma are deteriorated. When the refractive power of the rear-side positive lens become excessively small, an imaging performance is degraded due to a focus error at the time of manufacturing.

It is more preferable that the following conditional expression (6)' be satisfied instead of conditional expression (6).

$$0.4 \leq fG3pf/fG3pr \leq 0.7 \qquad (6)'$$

It is even more preferable that the following conditional expression (6)" be satisfied instead of conditional expression (6).

$$0.42 \leq fG3pf/fG3pr \leq 0.6 \qquad (6)''$$

In the objective optical system for endoscope according to the present embodiment, it is preferable that the front group include a cemented lens, and the cemented lens include a front-side negative lens, and the rear group include a rear-side positive lens, and the following conditional expression (7) be satisfied:

$$-1.1 \leq fG3nf/fG3 \leq -0.5 \qquad (7)$$

where, fG3nf denotes a focal length of the front-side negative lens, and fG3 denotes the focal length of the third lens group.

In the objective optical system for endoscope according to the present embodiment, the refractive power of the rear group is either equal to the refractive power of the front group or larger than the refractive power of the front group. By making the refractive power of the rear group larger than the refractive power of the front group, it is possible to vary a balance of the refractive power of the front group and the refractive power of the rear group. In this case, it is necessary to set appropriately the focal length of the negative lens in the front group. For such reason, it is preferable to satisfy conditional expression (7).

In a case of exceeding an upper limit value of conditional expression (7), the refractive power of the front-side negative lens becomes excessively large or the radius of curvature of the cemented surface becomes excessively small. When the refractive power of the front-side negative lens becomes excessively large, the coma and the chromatic aberration of magnification are corrected excessively. When the radius of curvature of the cemented surface becomes excessively small, lens processing becomes difficult.

In a case of falling below a lower limit value of conditional expression (7), the refractive power of the front-side negative lens becomes excessively small. Consequently, the coma and the chromatic aberration of magnification are corrected inadequately.

It is more preferable that the following conditional expression (7)' be satisfied instead of conditional expression (7).

$$-1 \leq fG3nf/fG3 \leq -0.55 \qquad (7)'$$

It is even more preferable that the following conditional expression (7)" be satisfied instead of conditional expression (7).

$$-0.9 \leq fG3nf/fG3 \leq -0.6 \qquad (7)''$$

In the objective optical system for endoscope according to the present embodiment, it is preferable that the front group include a cemented lens, and the cemented lens includes a front-side positive lens, and the rear group include a rear-side positive lens, and the following conditional expression (8) be satisfied:

$$0 \leq (rG3pff + rG3pfr)/(rG3pff - rG3pfr) \leq 0.41 \qquad (8)$$

where, rG3pff denotes a radius of curvature of an object-side surface of the front-side positive lens, and rG3pfr denotes a radius of curvature of an image-side surface of the front-side positive lens.

In the third lens group, it is desirable to converge a divergent light ray incident from the second lens group, and to make an arrangement such that an angle of incidence of a principal light ray incident eventually on an image plane becomes small. In other words, it is preferable to make the arrangement of the optical system the telecentric arrangement on the image side, or an arrangement closer to the telecentric arrangement.

The cemented lens in the front group converges the light ray incident from the second lens group, and the chromatic aberration has to be corrected in the cemented lens. Therefore, taking into consideration this point, it is necessary to set the radius of curvature of the front-side positive lens appropriately. For such reason, it is preferable that conditional expression (8) be satisfied.

In a case of exceeding an upper limit value of conditional expression (8), the radius of curvature of the object-side surface of the front-side positive lens becomes excessively large or the radius of curvature of the image-side surface becomes excessively small. When the radius of curvature of the object-side surface becomes excessively large, it is not possible to make small the angle of incidence of the principal light ray incident on the image plane. In other words, it is not possible to make the arrangement of the optical system the telecentric arrangement on the image side or the arrangement closer to the telecentric arrangement. In this case, a performance at the time of lens decentering such as shift is degraded. When the radius of curvature of the image-side surface becomes excessively small, the chromatic aberration is corrected excessively.

In a case of falling below a lower limit value of conditional expression (8), the radius of curvature of the object-side surface of the front-side positive lens becomes excessively small or the radius of curvature of the image-side surface of the front positive lens becomes excessively large. When the radius of curvature of the object-side surface of the front positive lens becomes excessively small, an occurrence of the coma and the astigmatism becomes substantial. As a result, an imaging performance is degraded. When the radius of curvature of image-side surface of the front positive lens becomes excessively large, the chromatic aberration is corrected excessively.

It is more preferable that the following conditional expression (8)' be satisfied instead of conditional expression (8).

$$0.15 \leq (rG3pff + rG3pfr)/(rG3pff - rG3pfr) \leq 0.41 \quad (8)'$$

In the objective optical system for endoscope according to the present embodiment, it is preferable that the front group include a cemented lens, and the cemented lens include a front-side positive lens, and the rear group include a rear-side positive lens, and the following conditional expression (9) be satisfied:

$$-0.6 \leq rG3pff/rG3prr \leq 0 \quad (9)$$

where, rG3pff denotes the radius of curvature of an object-side surface of the front-side positive lens, and rG3prr denotes a radius of curvature of an image-side surface of the rear-side positive lens.

As mentioned above, in the third lens group, it is desirable to make an arrangement such that the angle of incidence of the principal light ray incident eventually on the image plane becomes small. In other words, it is preferable to make the arrangement of the optical system the telecentric arrangement on the image side or the arrangement closer to the telecentric arrangement.

However, when such arrangement is made, the light-ray height at the third lens group becomes high. Consequently, the lens diameter also becomes large. For suppressing the increase in the lens diameter, it is preferable to make a convergence effect in the front group large. For such reason, it is preferable that conditional expression (9) is satisfied.

In a case of exceeding an upper limit value of conditional expression (9), one of the radius of curvature of the object-side surface of the front-side positive lens and the radius of curvature of the image-side surface of the rear-side positive lens becomes a radius of curvature for which the divergence effect occurs, or it is not possible to correct the coma and the astigmatism adequately. When the divergence effect at the lens surface becomes large, the lens diameter becomes large. Moreover, when the coma and the astigmatism are not corrected thoroughly, an imaging performance is degraded.

In a case of falling below a lower limit value of conditional expression (9), the radius of curvature of the object-side surface of the front-side positive lens becomes excessively large or the radius of curvature of the image-side surface of the rear-side positive lens becomes excessively small. When the radius of curvature of the object-side surface of the front-side positive lens becomes excessively large, the light-ray height at the third lens group becomes high. As a result, the lens diameter of the third lens group becomes large. When the radius of curvature of the image-side surface of the rear-side positive lens becomes excessively small, the astigmatism is deteriorated.

It is more preferable that the following conditional expression (9)' be satisfied instead of conditional expression (9).

$$0.55 \leq rG3pff/rG3prr \leq 0 \quad (9)'$$

In the objective optical system for endoscope according to the present embodiment, it is preferable to carryout a focus adjustment at the time of assembling by varying a distance between the front group and the rear group.

While assembling the objective optical system for endoscope, lenses are cased in lens frames that are determined in advance. In such initial assembled state, a position of the image plane is shifted from a position at the time of design due to Newton's error and lens-thickness error in each lens. The image pickup element for example, is disposed at an image position at the time of design. When the position of the image plane is shifted from the position at the time of design, a focused image is not formed on the image pickup surface. Therefore, the focus adjustment is carried out and the position of each lens is determined.

It is preferable to carry out the focus adjustment by varying the distance between the front group and the rear group. Accordingly, an amount of movement of the image position with respect to an amount of movement of a lens decreases. As a result, the focus adjustment at the time of assembling becomes easy.

Moreover, at the time of fixing the lens in the lens frame, an adhesive is to be used. When the amount of movement of the image position decreases with respect to the amount of movement of the lens, even when there is a shift in position of the lens at the time of hardening the adhesive, it is possible to make small the degradation of imaging performance due to the shift.

The rear group may be moved in a direction perpendicular to an optical axis. By doing so, it is possible to make small a difference in left and right of an angle of view, and a shift in the focusing position at a periphery of an image field. Moreover, it is possible to correct an asymmetric astigmatism.

In the objective optical system for endoscope according to the present embodiment, it is preferable to make the following arrangement for the object-side negative lens. Dirt and blood etc. are adhered to an object-side surface of the object-side negative lens during the observation. In this state, it is not possible to carry out a clear observation. Therefore, cleaning of the object-side surface of the object-side negative lens is carried out by water from a nozzle at a front end of the insertion portion.

When the object-side surface of the object-side negative lens has a convex shape, the dirt is hard to be removed at the time of cleaning. Moreover, when the object-side surface of the object-side negative lens has a concave shape, water is accumulated therein. Particularly, when the object-side surface of the object-side negative lens has a convex shape, the lens is susceptible to be scratched or cracked. Therefore, it is preferable that the shape of the object-side negative lens is planoconcave, and a flat surface is directed toward the object side.

Examples will be described below.

Example 1

Figure 2A:
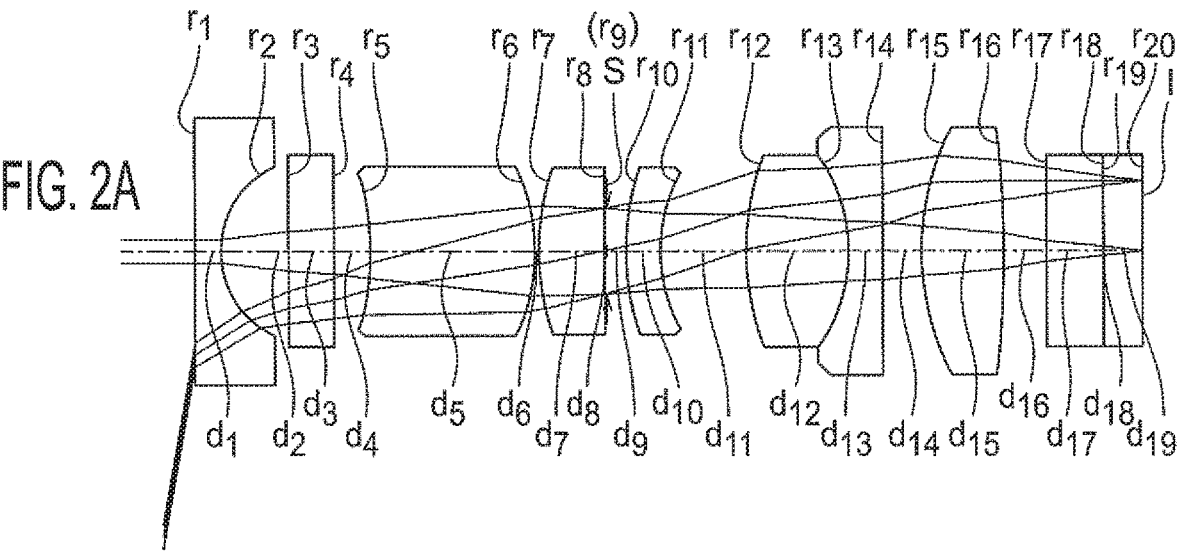
FIG. 2A and FIG. 2B are cross-sectional views of an objective optical system for endoscope of an example 1.
Figure 2B:
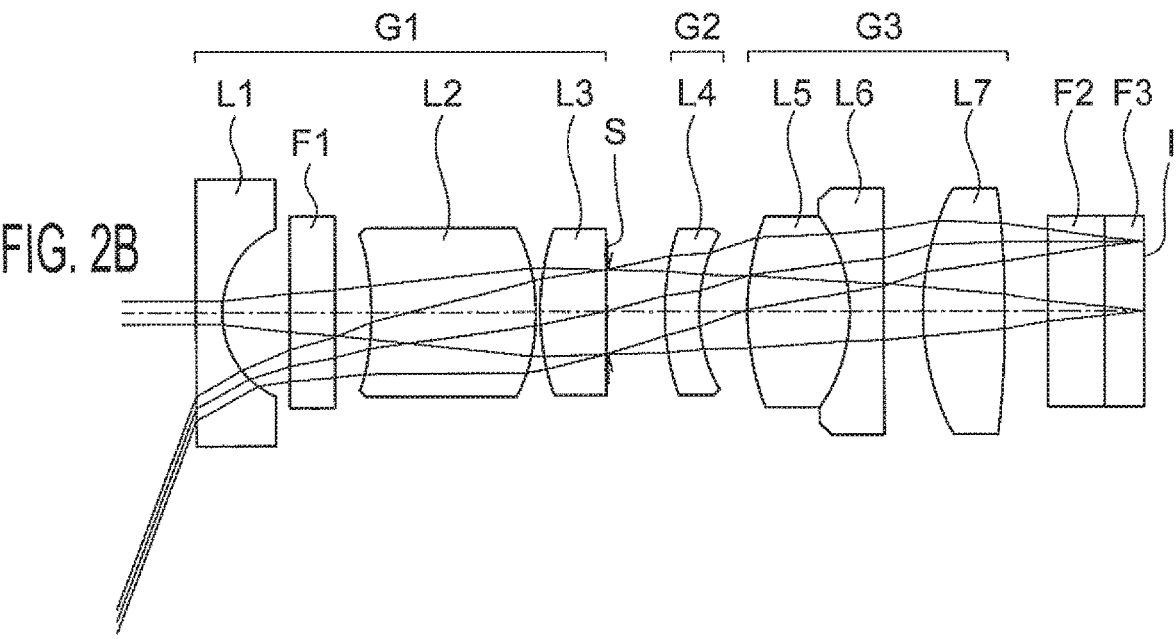

An objective optical system for endoscope according to an example 1 will be described below. FIG. 2A and FIG. 2B are lens cross-sectional views of the objective optical system for endoscope according to the example 1, where, FIG. 2A is a cross-sectional view in a normal observation state and FIG. 2B is a cross-sectional view in a close observation state.

The objective optical system for endoscope of the example 1 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a planoconvex positive lens L3.

The second lens group G2 includes a negative meniscus lens L3 having a convex surface directed toward the object side.

The third lens group G3 includes a biconvex positive lens L5, a planoconcave negative lens L6, and a biconvex positive lens L7. Here, the biconvex positive lens L5 and the planoconcave negative lens L6 form the cemented lens.

The front group includes the biconvex positive lens L5 and the planoconcave negative lens L6. The rear group includes the biconvex positive lens L7.

An aperture stop S is disposed between the first lens group G1 and the second lens group G2. More specifically, the aperture stop S is disposed near an image-side surface of the planoconvex positive lens L3.

An infrared absorbing filter F1 is disposed on the image side of the planoconcave negative lens L1. A cover glass F2, and a cover glass F3 of a CCD (charge coupled device), are disposed on the image side of the third lens group G3. The cover glass F2, and the cover glass F3 of the CCD, are cemented.

At the time of focusing, the second lens group G2 moves. At the time of focusing from an object point at a long distance to an object point at a close distance, the second lens group G2 moves toward the image side.

FIG. 3A, FIG. 3B, FIG. 3C, and FIG. 3D are aberration diagrams of a spherical aberration (SA), an astigmatism (AS), a distortion (DT), and a chromatic aberration of magnification (CC) respectively, in the normal observation state of the example 1. FIG. 3E, FIG. 3F, FIG. 3G, and FIG. 3H are aberration diagrams of a spherical aberration (SA), an astigmatism (AS), a distortion (DT), and a chromatic aberration of magnification (CC) respectively, in the close observation state of the example 1.

In each aberration diagram, a horizontal axis indicates an aberration amount. The unit of the aberration amount is mm for the spherical aberration, the astigmatism, and the chromatic aberration of magnification. Moreover, the unit of aberration amount is % for the distortion. Furthermore, FIY denotes an image height and the unit thereof is mm, and FNO denotes an F-number. The unit of wavelength of an aberration curve is nm. Same is true for the other examples.

Example 2

Figure 4A:
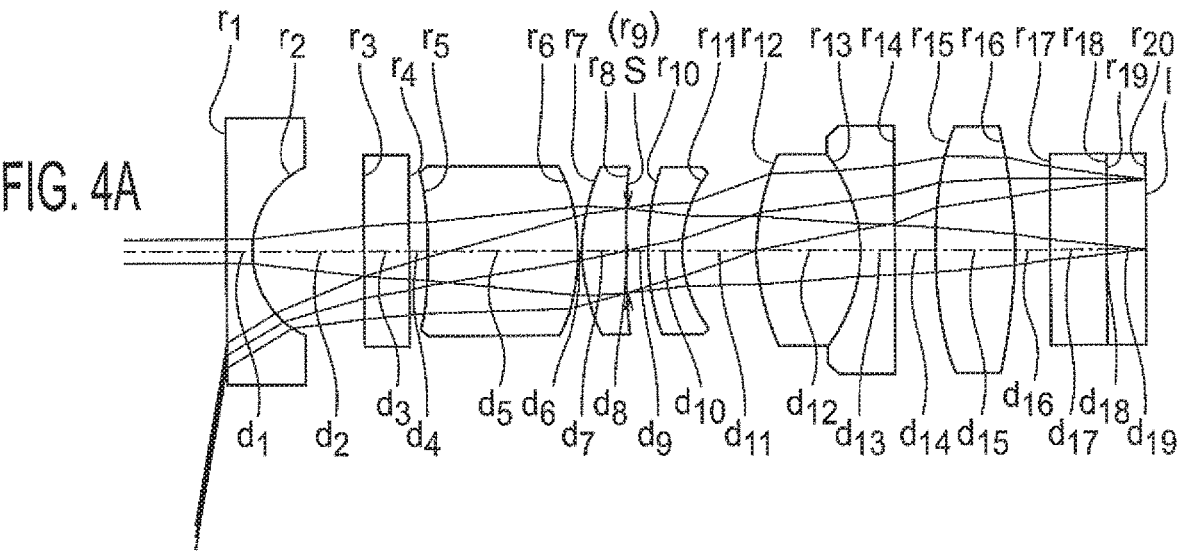
FIG. 4A and FIG. 4B are cross-sectional views of an objective optical system for endoscope of an example 2.
Figure 4B:
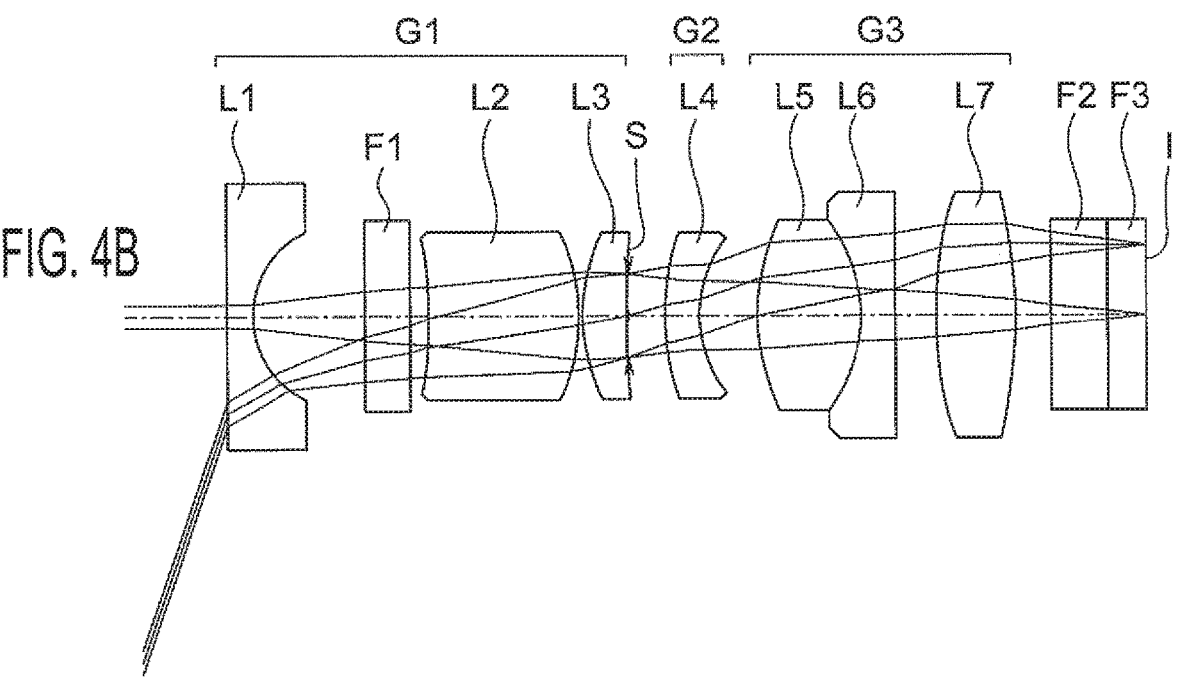

An objective optical system for endoscope according to an example 2 will be described below. FIG. 4A and FIG. 4B are lens cross-sectional views of the objective optical system for endoscope according to the example 2, where, FIG. 4A is a cross-sectional view in a normal observation state and FIG. 4B is a cross-sectional view in a close observation state.

The objective optical system for endoscope of the example 2 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a positive meniscus lens L3 having a convex surface directed toward the object side.

The second lens group G2 includes a negative meniscus lens L4 having a convex surface directed toward the object side.

The third lens group G3 includes a biconvex positive lens L5, a planoconcave negative lens L6, and a biconvex positive lens L7. Here, the biconvex positive lens L5 and the planoconcave negative lens L6 form the cemented lens.

The front group includes the biconvex positive lens L5 and the planoconcave negative lens L6. The rear group includes the biconvex positive lens L7.

An aperture stop S is disposed between the first lens group G1 and the second lens group G2. More specifically, the aperture stop S is disposed near an image-side surface of the positive meniscus lens L3.

An infrared absorbing filter F1 is disposed on the image side of the planoconcave negative lens L1. A cover glass F2, and a cover glass F3 of a CCD, are disposed on the image side of the third lens group G3. The cover glass F2, and the cover glass F3 of the CCD, are cemented.

At the time of focusing, the second lens group G2 moves. At the time of focusing from an object point at a long distance to an object point at a close distance, the second lens group G2 moves toward the image side.

FIG. 5A, FIG. 5B, FIG. 5C, and FIG. 5D are aberration diagrams of a spherical aberration (SA), an astigmatism (AS), a distortion (DT), and a chromatic aberration of magnification (CC) respectively, in the normal observation state of the example 2. FIG. 5E, FIG. 5F, FIG. 5G, and FIG. 5H are aberration diagrams of a spherical aberration (SA), an astigmatism (AS), a distortion (DT), and a chromatic aberration of magnification (CC) respectively, in the close observation state of the example 2.

Example 3

Figure 6A:
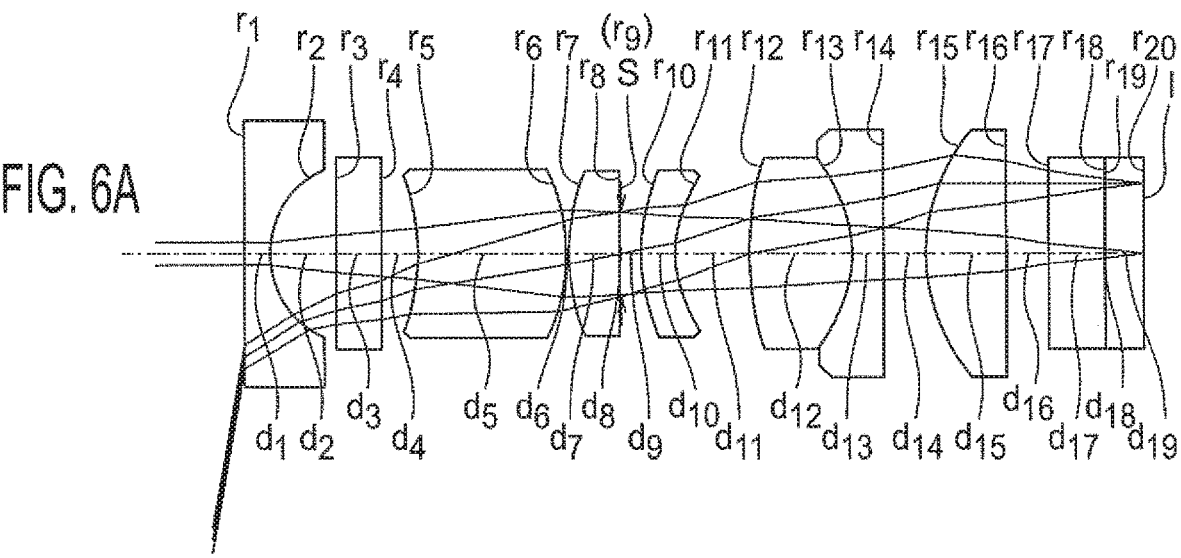
FIG. 6A and FIG. 6B are cross-sectional views of an objective optical system for endoscope of an example 3.
Figure 6B:
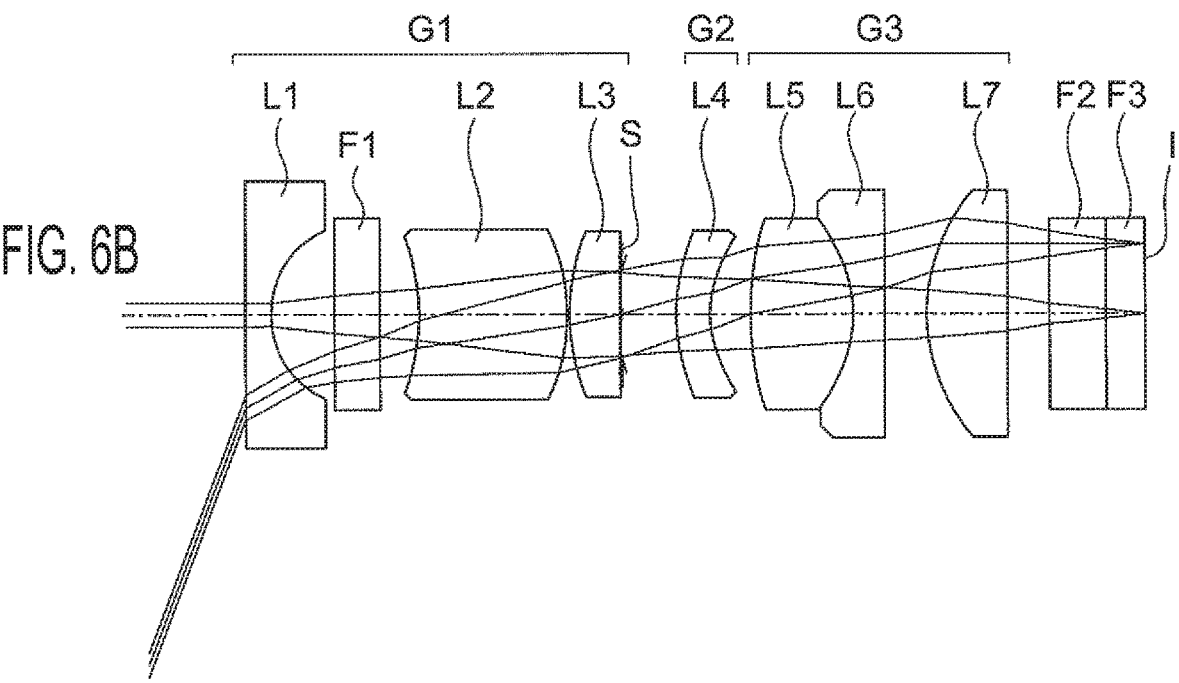

An objective optical system for endoscope according to an example 3 will be described below. FIG. 6A and FIG. 6B are lens cross-sectional views of the objective optical system for endoscope according to the example 3, where, FIG. 6A is a cross-sectional view in a normal observation state and FIG. 6B is a cross-sectional view in a close observation state.

The objective optical system for endoscope of the example 3 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a planoconvex positive lens L3.

The second lens group G2 includes a negative meniscus lens L4 having a convex surface directed toward the object side.

The third lens group G3 includes a biconvex positive lens L5, a planoconcave negative lens L6, and a biconvex positive lens L7. Here, the biconvex positive lens L5 and the planoconcave negative lens L6 form the cemented lens.

The front group includes the biconvex positive lens L5 and the planoconcave negative lens L6. The rear group includes the biconvex positive lens L7.

An aperture stop S is disposed between the first lens group G1 and the second lens group G2. More specifically, the aperture stop S is disposed near an image-side surface of the planoconvex positive lens L3.

An infrared absorbing filter F1 is disposed on the image side of the planoconcave negative lens L1. A cover glass F2, and a cover glass F3 of a CCD, are disposed on the image side of the third lens group G3. The cover glass F2, and the cover glass F3 of the CCD, are cemented.

At the time of focusing, the second lens group G2 moves. At the time of focusing from an object point at a long distance to an object point at a close distance, the second lens group G2 moves toward the image side.

FIG. 7A, FIG. 7B, FIG. 7C, and FIG. 7D are aberration diagrams of a spherical aberration (SA), an astigmatism (AS), a distortion (DT), and a chromatic aberration of magnification (CC) respectively, in the normal observation state of the example 3. FIG. 7E, FIG. 7F, FIG. 7G, and FIG. 7H are aberration diagrams of a spherical aberration (SA), an astigmatism (AS), a distortion (DT), and a chromatic aberration of magnification (CC) respectively, in the close observation state of the example 3.

Example 4

Figure 8A:
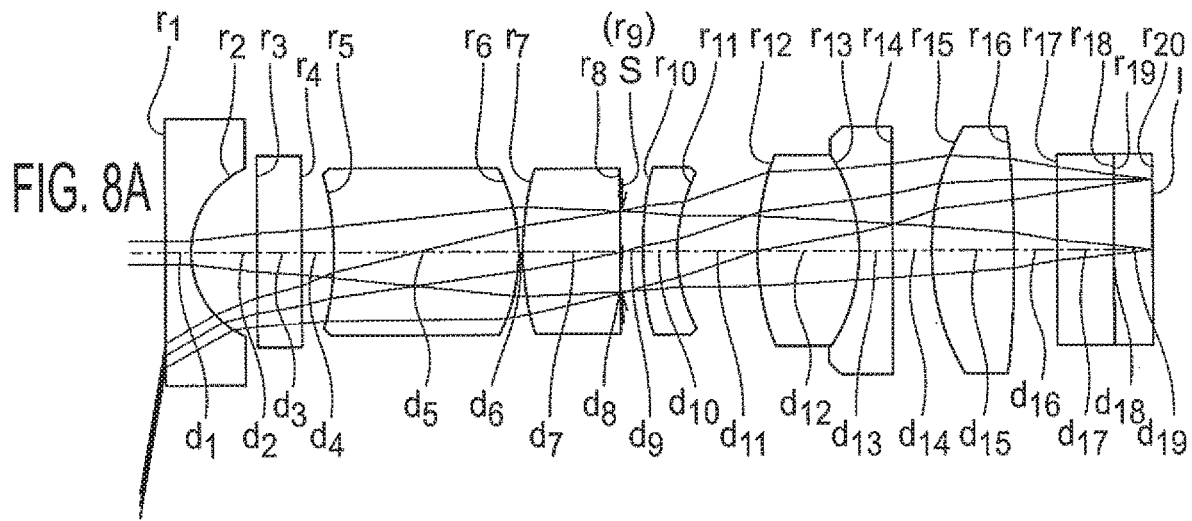
FIG. 8A and FIG. 8B are cross-sectional views of an objective optical system for endoscope of an example 4.
Figure 8B:
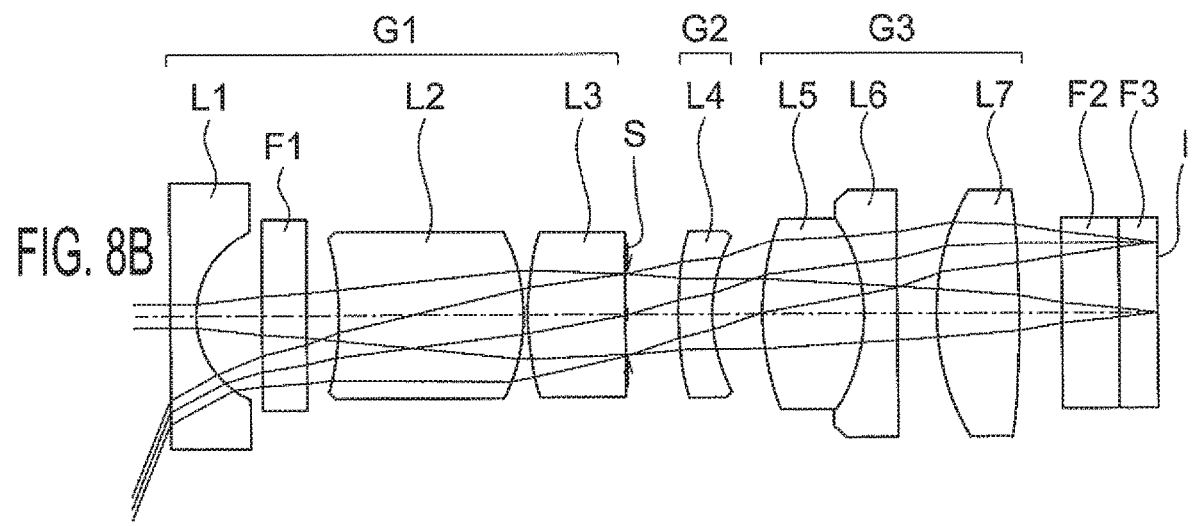

An objective optical system for endoscope according to an example 4 will be described below. FIG. 8A and FIG. 8B are lens cross-sectional views of the objective optical system for endoscope according to the example 4, where, FIG. 8A is a cross-sectional view in a normal observation state and FIG. 8B is a cross-sectional view in a close observation state.

The objective optical system for endoscope of the example 4 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a planoconvex positive lens L3.

The second lens group G2 includes a negative meniscus lens L4 having a convex surface directed toward the object side.

The third lens group G3 includes a biconvex positive lens L5, a planoconcave negative lens L6, and a biconvex positive lens L7. Here, the biconvex positive lens L5 and the planoconcave negative lens L6 form the cemented lens.

The front group includes the biconvex positive lens L5 and the planoconcave negative lens L6. The rear group includes the biconvex positive lens L7.

An aperture stop S is disposed between the first lens group G1 and the second lens group G2. More specifically, the aperture stop S is disposed near an image-side surface of the planoconvex positive lens L3.

An infrared absorbing filter F1 is disposed on the image side of the planoconcave negative lens L1. A cover glass F2, and a cover glass F3 of a CCD, are disposed on the image side of the third lens group G3. The cover glass F2, and the cover glass F3 of the CCD, are cemented.

At the time of focusing, the second lens group G2 moves. At the time of focusing from an object point at a long distance to an object point at a close distance, the second lens group G2 moves toward the image side.

FIG. 9A, FIG. 9B, FIG. 9C, and FIG. 9D are aberration diagrams of a spherical aberration (SA), an astigmatism (AS), a distortion (DT), and a chromatic aberration of magnification (CC) respectively, in the normal observation state of the example 4. FIG. 9E, FIG. 9F, FIG. 9G, and FIG. 9H are aberration diagrams of a spherical aberration (SA), an astigmatism (AS), a distortion (DT), and a chromatic aberration of magnification (CC) respectively, in the close observation state of the example 4.

Example 5

An objective optical system for endoscope according to an example 5 will be described below. FIG. 10A and FIG. 10B are lens cross-sectional views of the objective optical system for endoscope according to the example 5, where, FIG. 10A is a cross-sectional view in a normal observation state and FIG. 10B is a cross-sectional view in a close observation state.

The objective optical system for endoscope of the example 5 includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, and a biconvex positive lens L3.

The second lens group G2 includes a negative meniscus lens L4 having a convex surface directed toward the object side.

The third lens group G3 includes a biconvex positive lens L5, a planoconcave negative lens L6, and a biconvex positive lens L7. Here, the biconvex positive lens L5 and the planoconcave negative lens L6 form the cemented lens.

The front group includes the biconvex positive lens L5 and the planoconcave negative lens L6. The rear group includes the biconvex positive lens L7.

An aperture stop S is disposed between the first lens group G1 and the second lens group G2. More specifically, the aperture stop S is disposed near an image-side surface of the biconvex positive lens L3.

An infrared absorbing filter F1 is disposed on the image side of the planoconcave negative lens L1. A cover glass F2, and a cover glass F3 of a CCD, are disposed on the image side of the third lens group G3. The cover glass F2, and the cover glass F3 of the CCD, are cemented.

At the time of focusing, the second lens group G2 moves. At the time of focusing from an object point at a long distance to an object point at a close distance, the second lens group G2 moves toward the image side.

FIG. 11A, FIG. 11B, FIG. 11C, and FIG. 11D are aberration diagrams of a spherical aberration (SA), an astigmatism (AS), a distortion (DT), and a chromatic aberration of magnification (CC) respectively, in the normal observation state of the example 5. FIG. 11E, FIG. 11F, FIG. 11G, and FIG. 11H are aberration diagrams of a spherical aberration (SA), an astigmatism (AS), a distortion (DT), and a chromatic aberration of magnification (CC) respectively, in the close observation state of the example 5.

Numerical data of each example described above is shown below. In Surface data, in symbols, r denotes radius of curvature of each lens surface, d denotes a distance between respective lens surfaces, ne denotes a refractive index of each lens for a e-line, vd denotes an Abbe number for each lens.

In various data, f denotes a focal length in e-line, FNO. denotes an F number, ω denotes a half angle of view, and IH denotes an image height.

Example 1

Unit mm

Surface data

| Surface no. | r | d | ne | vd |
|---|---|---|---|---|
| 1 | ∞ | 0.2297 | 1.88815 | 40.76 |
| 2 | 0.8041 | 0.5732 | | |
| 3 | ∞ | 0.3828 | 1.52300 | 65.13 |
| 4 | ∞ | 0.3029 | | |
| 5 | −2.2902 | 1.3872 | 1.48915 | 70.23 |
| 6 | −1.5783 | 0.0296 | | |
| 7 | 2.3329 | 0.5694 | 1.65222 | 33.79 |
| 8 | ∞ | 0.0191 | | |
| 9(Stop) | ∞ | Variable | | |
| 10 | 2.4190 | 0.2871 | 1.51977 | 52.43 |
| 11 | 1.3873 | Variable | | |
| 12 | 2.3608 | 0.8614 | 1.77621 | 49.60 |
| 13 | −1.4302 | 0.2871 | 1.93429 | 18.90 |
| 14 | ∞ | 0.3254 | | |
| 15 | 2.2688 | 0.6890 | 1.70042 | 48.52 |
| 16 | −9.1628 | 0.3592 | | |
| 17 | ∞ | 0.4785 | 1.51825 | 64.14 |
| 18 | ∞ | 0.0100 | 1.51500 | 64.00 |
| 19 | ∞ | 0.3350 | 1.50700 | 63.26 |
| 20(Image pickup surface) | ∞ | | | |

Various data

| | Normal observation State | Close observation state |
|---|---|---|
| f | 0.613 | 0.633 |
| Fno | 2.99 | 3.10 |
| ω | 80.2 | 70.3 |
| IH | 0.6 | |
| d9 | 0.1626 | 0.4713 |
| d11 | 0.7242 | 0.4155 |

Example 2

Unit mm

Surface data

| Surface no. | r | d | ne | vd |
|---|---|---|---|---|
| 1 | ∞ | 0.2297 | 1.88815 | 40.76 |
| 2 | 0.8044 | 0.9483 | | |
| 3 | ∞ | 0.3829 | 1.52300 | 65.13 |
| 4 | ∞ | 0.1471 | | |
| 5 | −3.7942 | 1.2817 | 1.48915 | 70.23 |
| 6 | −1.5278 | 0.0296 | | |
| 7 | 1.7274 | 0.3787 | 1.65222 | 33.79 |
| 8 | 7.5054 | 0.0191 | | |
| 9(Stop) | ∞ | Variable | | |
| 10 | 2.1671 | 0.2872 | 1.58482 | 40.75 |
| 11 | 1.0977 | Variable | | |
| 12 | 1.9205 | 0.8807 | 1.73234 | 54.68 |
| 13 | −1.2825 | 0.2872 | 1.93429 | 18.90 |
| 14 | ∞ | 0.3430 | | |
| 15 | 3.8561 | 0.6595 | 1.88815 | 40.76 |
| 16 | −3.8561 | 0.2840 | | |
| 17 | ∞ | 0.4786 | 1.51825 | 64.14 |
| 18 | ∞ | 0.0100 | 1.51500 | 64.00 |
| 19 | ∞ | 0.3400 | 1.50700 | 63.26 |
| 20(Image pickup surface) | ∞ | | | |

Various data

| | Normal observation State | Close observation state |
|---|---|---|
| f | 0.615 | 0.631 |
| Fno | 2.98 | 3.07 |
| ω | 80.2 | 72.0 |
| IH | 0.6 | |
| d9 | 0.1628 | 0.3078 |
| d11 | 0.6289 | 0.4839 |

Example 3

Unit mm

Surface data

| Surface no. | r | d | ne | vd |
|---|---|---|---|---|
| 1 | ∞ | 0.2297 | 1.88815 | 40.76 |
| 2 | 0.8041 | 0.5253 | | |
| 3 | ∞ | 0.3828 | 1.52300 | 65.13 |
| 4 | ∞ | 0.3176 | | |
| 5 | −1.8502 | 1.2432 | 1.48915 | 70.23 |
| 6 | −1.5727 | 0.0296 | | |
| 7 | 1.9414 | 0.4374 | 1.65222 | 33.79 |
| 8 | ∞ | 0.0191 | | |
| 9(Stop) | ∞ | Variable | | |
| 10 | 1.8021 | 0.2871 | 1.51977 | 52.43 |
| 11 | 1.1652 | Variable | | |
| 12 | 2.9320 | 0.8614 | 1.77621 | 49.60 |
| 13 | −1.2343 | 0.2871 | 1.93429 | 18.90 |
| 14 | ∞ | 0.3254 | | |
| 15 | 1.6266 | 0.6890 | 1.70042 | 48.52 |
| 16 | −882.1583 | 0.3437 | | |
| 17 | ∞ | 0.4785 | 1.51825 | 64.14 |
| 18 | ∞ | 0.0096 | 1.51500 | 64.00 |
| 19 | ∞ | 0.3349 | 1.50700 | 63.26 |
| 20(Image pickup surface) | ∞ | | | |

Various data

| | Normal observation State | Close observation state |
|---|---|---|
| f | 0.626 | 0.643 |
| Fno | 3.00 | 3.10 |
| 2ω | 79.4 | 70.3 |
| IH | 0.6 | |
| d9 | 0.1626 | 0.4829 |
| d11 | 0.6268 | 0.3065 |

Example 4

| Unit mm | | | | |
|---|---|---|---|---|
| Surface data | | | | |
| Surface no. | r | d | ne | vd |
| 1 | ∞ | 0.2297 | 1.88815 | 40.76 |
| 2 | 0.8041 | 0.5688 | | |
| 3 | ∞ | 0.3828 | 1.52300 | 65.13 |
| 4 | ∞ | 0.2539 | | |
| 5 | −2.8149 | 1.5598 | 1.48915 | 70.23 |
| 6 | −1.5561 | 0.0296 | | |
| 7 | 2.5499 | 0.8444 | 1.65222 | 33.79 |
| 8 | ∞ | 0.0191 | | |
| 9(Stop) | ∞ | Variable | | |
| 10 | 3.1315 | 0.2871 | 1.51977 | 52.43 |
| 11 | 1.4515 | Variable | | |
| 12 | 2.2357 | 0.8614 | 1.77621 | 49.60 |
| 13 | −1.4888 | 0.2871 | 1.93429 | 18.90 |
| 14 | ∞ | 0.3254 | | |
| 15 | 2.2538 | 0.6890 | 1.70042 | 48.52 |
| 16 | −9.1628 | 0.3553 | | |
| 17 | ∞ | 0.4785 | 1.51825 | 64.14 |
| 18 | ∞ | 0.0100 | 1.51500 | 64.00 |
| 19 | ∞ | 0.3400 | 1.50700 | 63.26 |
| 20(Image pickup surface) | ∞ | | | |

| Various data | | |
|---|---|---|
| | Normal observation State | Close observation state |
| f | 0.616 | 0.641 |
| Fno | 3.03 | 3.17 |
| 2ω | 80.2 | 69.1 |
| IH | 0.6 | |
| d9 | 0.1626 | 0.4424 |
| d11 | 0.6794 | 0.3997 |

Example 5

| Unit mm | | | | |
|---|---|---|---|---|
| Surface data | | | | |
| Surface no. | r | d | ne | vd |
| 1 | ∞ | 0.2297 | 1.88815 | 40.76 |
| 2 | 0.8041 | 0.4744 | | |
| 3 | ∞ | 0.3828 | 1.52300 | 65.13 |
| 4 | ∞ | 0.2040 | | |
| 5 | −2.2719 | 1.2668 | 1.48915 | 70.23 |
| 6 | −2.4215 | 0.2297 | | |
| 7 | 3.4112 | 0.5550 | 1.65222 | 33.79 |
| 8 | −3.1575 | 0.0191 | | |
| 9(Stop) | ∞ | Variable | | |
| 10 | 2.4533 | 0.2871 | 1.51977 | 52.43 |
| 11 | 1.4938 | Variable | | |
| 12 | 2.3944 | 0.8614 | 1.77621 | 49.60 |
| 13 | −1.3554 | 0.2871 | 1.93429 | 18.90 |
| 14 | ∞ | 0.3254 | | |
| 15 | 2.3300 | 0.6890 | 1.70042 | 48.52 |
| 16 | −9.1628 | 0.4097 | | |
| 17 | ∞ | 0.4785 | 1.51825 | 64.14 |
| 18 | ∞ | 0.0100 | 1.51500 | 64.00 |
| 19 | ∞ | 0.3400 | 1.50700 | 63.26 |
| 20(Image pickup surface) | ∞ | | | |

| Various data | | |
|---|---|---|
| | Normal observation State | Close observation state |
| f | 0.610 | 0.634 |
| Fno | 2.97 | 3.10 |

-continued

| Unit mm | | |
|---|---|---|
| ω | 80.2 | 69.3 |
| IH | 0.6 | |
| d9 | 0.1626 | 0.5820 |
| d11 | 0.7775 | 0.3582 |

The values of conditional expressions (1) to (9) from the first example to the fifth example are shown below.

| Conditional expression | Example1 | Example2 | Example3 |
|---|---|---|---|
| (1-1)fG3f/fG3r | 1.59 | 1.74 | 2.82 |
| (1-2)dG3fr/dG3r | 0.47 | 0.52 | 0.47 |
| (2)fG1/fG3r | 0.61 | 0.51 | 0.66 |
| (3)fG2/fG3f | −1.63 | −1.07 | −1.15 |
| (4-1)fc/rc | −2.96 | −3.07 | 5.29 |
| (4-2)fG2/fG3 | −3.47 | −2.26 | −3.73 |
| (5-1)fG1/fG23 | 0.72 | 0.53 | 0.65 |
| (5-2)f/rG1nr | 0.76 | 0.76 | 0.78 |
| (6)fG3pf/fG3pr | 0.48 | 0.53 | 0.53 |
| (7)fG3nf/fG3 | −0.77 | −0.73 | −0.66 |
| (8)(rG3pff + rG3pfr)/(rG3pff − rG3pfr) | 0.25 | 0.20 | 0.41 |
| (9)rG3pff/rG3prr | −0.26 | −0.50 | 0.00 |

| Conditional expression | Example4 | Example5 |
|---|---|---|
| (1-1)fG3f/fG3r | 1.46 | 1.63 |
| (1-2)dG3fr/dG3r | 0.47 | 0.47 |
| (2)fG1/fG3r | 0.58 | 0.66 |
| (3)fG2/fG3f | −1.43 | −1.85 |
| (4-1)fc/rc | −2.59 | −3.27 |
| (4-2)fG2/fG3 | −2.87 | −4.01 |
| (5-1)fG1/fG23 | 0.69 | 0.79 |
| (5-2)f/rG1nr | 0.77 | 0.76 |
| (6)fG3pf/fG3pr | 0.48 | 0.46 |
| (7)fG3nf/fG3 | −0.83 | −0.71 |
| (8)(rG3pff + rG3pfr)/(rG3pff − rG3pfr) | 0.20 | 0.28 |
| (9)rG3pff/rG3prr | −0.24 | −0.26 |

According to each example, it is possible to provide an objective optical system for endoscope which has a small F-number, a small size, and a high imaging performance, and which is strong with respect to manufacturing errors.

Various embodiments of the present invention were described above. However, the present invention is not restricted to the embodiments described above, and embodiments in which arrangements of the embodiments described above are combined appropriately without departing from the scope of the invention are also within the scope of the present invention.

As described heretofore, the present invention is suitable for an objective optical system for endoscope which has a small F-number, a small size, and a high imaging performance, and which is strong with respect to the manufacturing error.

What is claimed is:

1. An objective optical system for endoscope, comprising in order from an object side:
   a first lens group having a positive refractive power;
   a second lens group having a negative refractive power; and
   a third lens group having a positive refractive power, wherein
   at a time of focusing to an object point at a short distance, the first lens group and the third lens group are fixed, and, the second lens group moves, and the third lens group consists of a front group having a positive refractive power and a rear group having a positive refractive power, and the front group includes one cemented lens and the rear group includes one single lens, and the following conditional expressions (1-1), (1-2), (4-1), and (4-2) are satisfied:

$$1 \leq fG3f/fG3r \leq 5 \quad (1\text{-}1)$$

$$0.1 \leq dG3fr/dG3r \leq 1 \quad (1\text{-}2)$$

$$-8 \leq fc/rc \leq -2 \quad (4\text{-}1)$$

$$-7 \leq fG2/fG3 \leq -2 \quad (4\text{-}2)$$

where, fG3f denotes a focal length of the front group, fG3r denotes a focal length of the rear group, dG3fr denotes a distance along an optical axis from a surface nearest to an image of the front group up to a surface nearest to an object of the rear group, dG3r denotes a total thickness along the optical axis of the rear group, fc denotes a focal length of the cemented lens, rc denotes a radius of curvature of a cemented surface of the cemented lens, fG2 denotes a focal length of the second lens group, and fG3 denotes a focal length of the third lens group.

2. The objective optical system for endoscope according to claim 1, wherein the following conditional expression (2) is satisfied:

$$0.42 \leq fG1/fG3r \leq 0.9 \quad (2)$$

where, fG1 denotes a focal length of the first lens group, and fG3r denotes the focal length of the rear group.

3. The objective optical system for endoscope according to claim 1, wherein the following conditional expression (3) is satisfied:

$$-2 \leq fG2/fG3f \leq -1.05 \quad (3)$$

where, fG2 denotes the focal length of the second lens group, and fG3f denotes the focal length of the front group.

4. The objective optical system for endoscope according to claim 1, wherein the first lens group includes an object-side negative lens which is disposed nearest to the object, and the following conditional expressions (5-1) and (5-2) are satisfied:

$$0.5 \leq fG1/fG23 \leq 1 \quad (5\text{-}1)$$

$$0.2 \leq f/rG1nr \leq 1 \quad (5\text{-}2)$$

where, fG1 denotes a focal length of the first lens group, fG23 denotes a combined focal length of the second lens group and the third lens group, f denotes a focal length of the overall objective optical system for endoscope, and rG1nr denotes a radius of curvature of an image-side surface of the object-side negative lens, and here the combined focal length and the focal length of the overall objective optical system for endoscope are focal lengths in a normal state.

5. The objective optical system for endoscope according to claim 1, wherein the cemented lens includes a front-side positive lens, and the rear group consists of a rear-side positive lens, and the following conditional expression (6) is satisfied:

$$0.38 \leq fG3pf/fG3pr \leq 0.9 \quad (6)$$

where, fG3pf denotes a focal length of the front-side positive lens, and fG3pr denotes a focal length of the rear-side positive lens.

6. The objective optical system for endoscope according to claim 1, wherein the cemented lens includes a front-side negative lens, and the rear group consists of a rear-side positive lens, and the following conditional expression (7) is satisfied:

$$-1.1 \leq fG3nf/fG3 \leq -0.5 \quad (7)$$

where, fG3nf denotes a focal length of the front-side negative lens, and fG3 denotes a focal length of the third lens group.

7. The objective optical system for endoscope according to claim 1, wherein the cemented lens includes a front-side positive lens, and the rear group consists of a rear-side positive lens, and the following conditional expression (8) is satisfied $$0 \leq (rG3pff + rG3pfr)/(rG3pff - rG3pfr) \leq 0.41 \quad (8)$$

where, rG3pff denotes a radius of curvature of an object-side surface of the front-side positive lens, and rG3pfr denotes a radius of curvature of an image-side surface of the front-side positive lens.

8. The objective optical system for endoscope according to claim 1, wherein the cemented lens includes a front-side positive lens, and the rear group consists of a rear-side positive lens, and the following conditional expression (9) is satisfied:

$$-0.6 \leq rG3pff/rG3prr \leq 0 \quad (9)$$

where, rG3pff denotes a radius of curvature of an object-side surface of the front positive lens, and rG3prr denotes a radius of curvature of an image-side surface of the rear positive lens.

9. The objective optical system for endoscope according to claim 1, wherein a focus adjustment at a time of assembling is carried out by varying a distance between the front group and the rear group.

* * * * *